United States Patent
Nan et al.

(10) Patent No.: US 8,426,606 B2
(45) Date of Patent: Apr. 23, 2013

(54) 2',2-BISTHIAZOLE NON-NUCLEOSIDE COMPOUNDS, PREPARATION METHODS, PHARMACEUTICAL COMPOSITIONS AND USES AS HEPATITIS VIRUS INHIBITORS THEREOF

(75) Inventors: Fajun Nan, Shanghai (CN); Jianping Zuo, Shanghai (CN); Yangming Zhang, Shanghai (CN); Wei Tang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 13/636,488

(22) PCT Filed: Mar. 16, 2011

(86) PCT No.: PCT/CN2011/071851
§ 371 (c)(1),
(2), (4) Date: Nov. 15, 2012

(87) PCT Pub. No.: WO2011/116663
PCT Pub. Date: Sep. 29, 2011

(65) Prior Publication Data
US 2013/0059895 A1    Mar. 7, 2013

(30) Foreign Application Priority Data
Mar. 24, 2010    (CN) .......................... 2010 1 0131636

(51) Int. Cl.
C07D 417/04    (2006.01)
A61K 31/427    (2006.01)

(52) U.S. Cl.
USPC .......................................... 548/200; 514/365

(58) Field of Classification Search .................... 548/200
See application file for complete search history.

(56) References Cited

U.S. PATENT DOCUMENTS
2010/0056569 A1* 3/2010 Nan et al. ...................... 514/314

FOREIGN PATENT DOCUMENTS
CN    101443330 A    5/2009
WO    2007147336 A1    12/2007

OTHER PUBLICATIONS

International Search Report mailed Jun. 23, 2011 issued in International Patent Application No. PCT/CN2011/071851.

* cited by examiner

*Primary Examiner* — Laura L. Stockton
(74) *Attorney, Agent, or Firm* — Ping Wang; Andrews Kurth, LLP

(57) ABSTRACT

The present disclosure belongs to the field of pharmaceutical chemistry, and relates to a class of 2',2-bisthiazole non-nucleoside compounds of following formula I, the preparation method and the pharmaceutical composition thereof. The compounds have both the anti-HBV and anti-HCV activities and are useful in treating hepatitides B and C. Pharmacokinetic tests showed the compounds have good bioavailability.

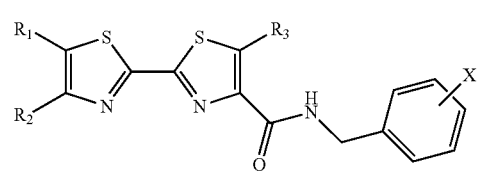

18 Claims, No Drawings

2',2-BISTHIAZOLE NON-NUCLEOSIDE COMPOUNDS, PREPARATION METHODS, PHARMACEUTICAL COMPOSITIONS AND USES AS HEPATITIS VIRUS INHIBITORS THEREOF

TECHNICAL FIELD

The present disclosure belongs to the field of pharmaceutical chemistry. In particular, the present invention relates to a class of 2',2-bisthiazole non-nucleoside compounds having an anti-HBV (Hepatitis B Virus) and anti-HCV (Hepatitis C Virus) activities, which can be used in treating hepatitides B and C, the preparation method thereof and the pharmaceutical composition comprising the same.

BACKGROUND ART

Viral hepatitides are internationally recognized tough questions in therapeutics up to now. Also, they are a class of hepatitides that are the most common and harmful with serious infectivity. In general, viruses leading to hepatitis are mainly divided into five types, i.e., types A, B, C, D and E. Among them, hepatitis A and E viruses infect intestinally, and their contamination in water source or food may result in pandemic infection. But hepatitides A and E will neither develop into chronic hepatitis, nor induce hepatocirrhosis, and patients recovering from them will gain a lifelong immunity. Viral hepatitides B, C and D are transmitted through blood, and a few of patients are infected by close contact with patient's saliva, semen, milk or the like, such as the infection between couples or mother and infant. Among the viral hepatitides, more than 80% of the acute infection with hepatitis B virus (HBV), hepatitis C virus (HCV) and hepatitis D virus (HDV) will progress to be chronic, wherein about 20% of them may possibly develop into hepatocirrhosis if suffered from persistent infection, and about 1% to about 5% of them may turn into liver cancer.

China has a high morbidity of viral hepatitides, there are 120 millions of hepatitis B virus carriers in China, and it is estimated that economic loss directly caused by viral hepatitides is about 30 to 50 billion RMB each year. While hepatitis C has a tendency of global prevalence and is the leading cause for the end-stage liver diseases in Europe, America and Japan. According to the statistics of WHO, the global infection rate of HCV is about 3%, and thus it is estimated that about 170 millions people have been infected with HCV, and about 35 thousands new cases of hepatitis C develop each year. A nationwide seroepidemiological investigation in China showed that the ratio of a person having anti-HCV antibodies in a general population was 3.2%.

HBV and HCV belong to different viral genera respectively, although they both belong to the hepatitis virus and have a similar route of infection. HBV belongs to the hepadnaviridae family and is made of a partially double-stranded circular DNA, while HCV belongs to the flaviviridae family and is a positive-sense single-strand RNA virus. At present, clinical anti-HBV drugs are mainly nucleoside drugs, such as lamivudine, famciclovir, lobucavir, adefovir dipivoxiil, FTC (2',3'-dideoxy-5-fluoro-3'-thiacytidine), FMAU (1-(2-fluoro-5-methyl-beta,L-arabinofuranosyl)uracil), FDDC (5-fluoro-2',3'-dideoxycytidine) BMS 200475 (9-[4-hydroxy-3-(hydroxymethyl)-2-methylenecyclopentyl]guanine), entacavir and the like. Since HBV and HCV belong to different viral genera, the existing anti-HBV drugs can not be used for treating Hepatitis C. So far, no effective small molecule drugs for HCV can be used in clinic. Presently, the most effective therapeutic regimen for HCV is the combined administration of interferon and broad-spectrum antiviral agent, such as interferon and ribavirin. But such combined administration only has a sustainable curative effect of less than 40% with serious adverse effect.

Therefore, as, it is always a focus for domestic and foreign pharmaceutical scientists to explore and develop a drug for treatment of viral hepatitides.

International application No. PCT/CN2007/001861 (International Publication No. WO 2007/147336), which is a previous international patent application of the present applicant, discloses a class of heterocyclic non-nucleoside compounds and the anti-HBV bioactivity thereof, and the compounds are useful for treating viral hepatitis B. However, the subsequent research reveals that some of the compounds exhibit poor pharmacokinetic parameters, especially bioavailability. For example, the oral bioavailability of Compound W28F in male rats (10 mg/kg) is only 2.80%. Thereby, there is an urgent demand to further modify the compounds so as to improve their bioavailability while maintaining their strong antiviral activity.

The present applicant incorporated a hydroxyl, a halogen atom or a double bond into the side chain at 5-site of thiazole ring of the 2',2-bisthiazole non-nucleoside compounds among the above compounds based on the original structure. The obtained compounds not only retain the same anti-HBV bioactivity as the original ones, but also show effectively improved bioavailability. Extensive research reveals that, besides the anti-HBV bioactivity, such novel 2',2-bisthiazole non-nucleoside compounds have an anti-HCV bioactivity.

DISCLOSURE OF THE INVENTION

Therefore, one object of the present disclosure is to provide a novel 2',2-bisthiazole non-nucleoside compound.

Another object of the present disclosure is to provide a preparation method for the 2',2-bisthiazole non-nucleoside compound of the present application.

Yet another object of the present disclosure is to provide a pharmaceutical composition of an HBV and/or HCV inhibitor, which comprise the 2',2-bisthiazole non-nucleoside compound of the present invention as an active component.

Still another object of the present disclosure is to provide a use of the 2',2-bisthiazole non-nucleoside compound of the present invention in preparation of a drug for treating viral hepatitis B and/or viral hepatitis C.

Still another object of the present disclosure is to provide a method for treatment of viral hepatitis B or viral hepatitis C.

According to one aspect of the present disclosure, provided is a 2',2-bisthiazole non-nucleoside compound of formula I:

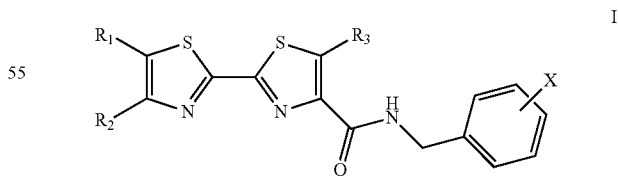

wherein,
$R_1$ and $R_2$ are each independently H or $C_1$-$C_4$ alkyl, and preferably, $R_1$ is H, methyl or ethyl, $R_2$ is H,
$R_3$ is $C_1$-$C_6$ alkyl substituted by at least one hydroxyl group, $C_1$-$C_6$ alkyl substituted by at least one $C_1$-$C_6$ alkoxyl group, $C_1$-$C_6$ alkyl substituted by at least one halogen atom, $C_2$-$C_6$ alkenyl, $C_2$-$C_6$ alkenyl substituted by at least one hydroxyl group or at least one halogen atom, preferably, $R_3$ is $C_1$-$C_5$ alkyl substituted by one or two hydroxyl groups, $C_1$-$C_5$ alkyl substituted by one or two $C_1$-$C_4$ alkoxyl groups, $C_1$-$C_5$ alkyl substituted by one fluorine, chlorine or bromine atom, methylpropenyl, methylolpropenyl or fluomethylpropenyl, and most preferably, $R_3$ is $C_4$ alkyl substituted by one or two hydroxyl groups, $C_4$ alkyl substituted by one or two $C_1$-$C_4$ alkoxyl groups, $C_4$ fluoroalkyl, 2-methylpropenyl, 2-methylolpropenyl or 2-fluomethylpropenyl, X is a halogen atom, preferably F, and most preferably F at 4-site.

The following definitions are made in the present disclosure. The alkyl includes linear or branched alkyl, the alkenyl includes linear or branched alkenyl and the halogen includes F, Cl, Br and I.

The 2',2-bisthiazole non-nucleoside compound of the present disclosure is most preferably one selected from the group consisting of

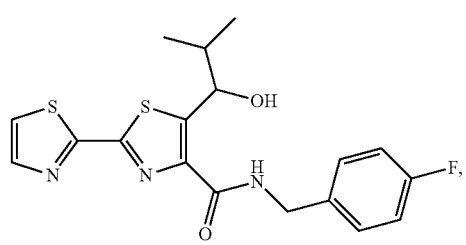

391-1

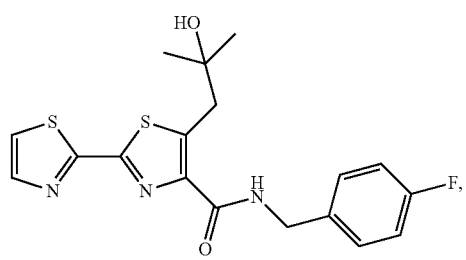

391-2

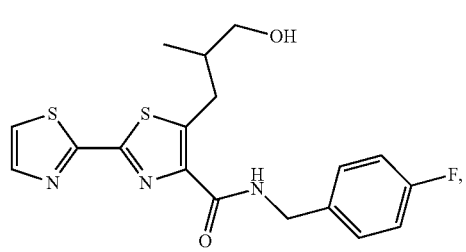

391-3

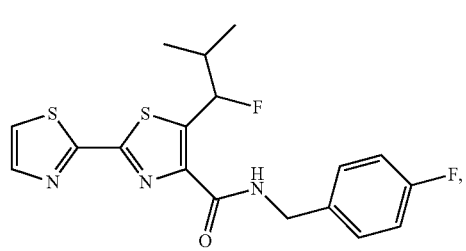

393-1

-continued

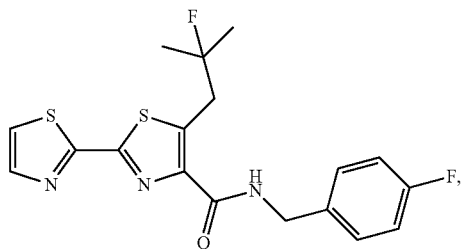

393-2

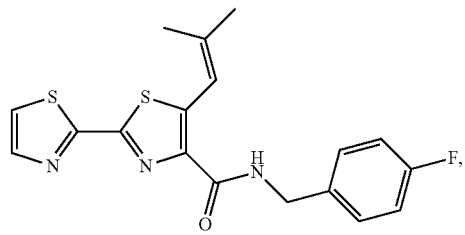

373

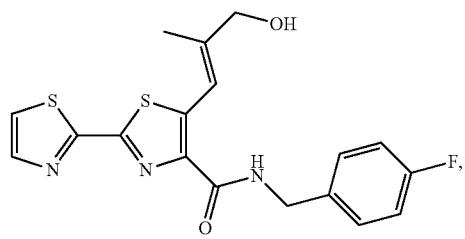

389

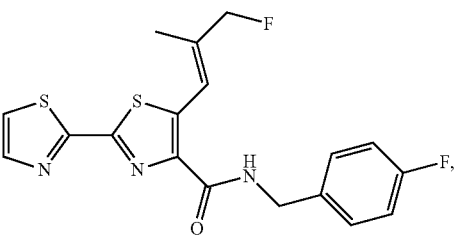

391-F

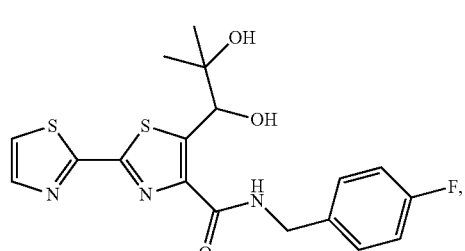

407

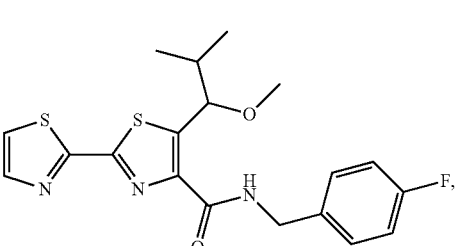

405-1

Me-373

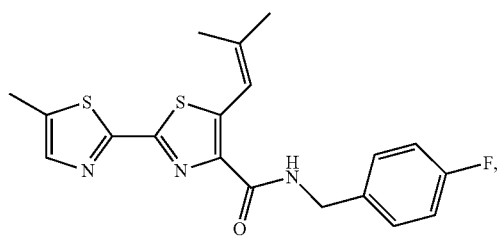

Me-391-1

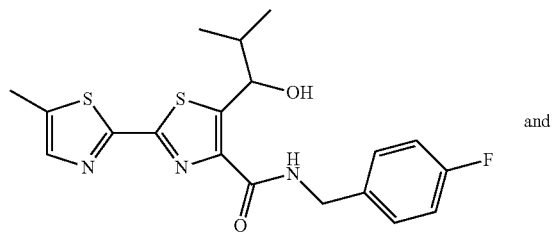

and

Me-393-1

The 2',2-bisthiazole non-nucleoside compound of the present disclosure can be prepared from an intermediate 4 as a starting material, which may be synthesized according to the following scheme (scheme I) disclosed in International Application No. PCT/CN2007/001861 (International Publication No. WO 2007/147336):

Scheme I

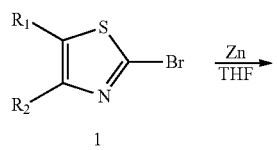

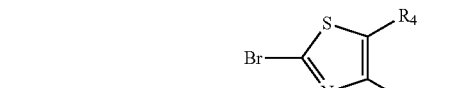

wherein, $R_1$ and $R_2$ is defined as above, and $R_4$ is $C_1$-$C_6$ alkyl.

In particular, the intermediate 2-bromo-thiazole 1 reacts with an activated zinc powder to produce a zinc reagent, which then reacts with another 2-bromo-thiazole intermediate 3 to produce an intermediate methyl 2',2-bisthiazolecarboxylate 4 through an Negishi coupling reaction in the present of palladium acetate.

Starting from the intermediate methyl 2',2-bisthiazolecarboxylate 4, various intermediate methyl 2',2-bisthiazolecarboxylates 4a-4i wherein the side chains are substituted with hydroxyl, alkoxyl or halogen atom (such as fluorine atom) can be prepared through a series of group transformation, as illustrated by the case that $R_4$ is isobutyl group (scheme II), which does not have any specific limitation on the present invention.

The intermediate methyl 5-isobutyl-2'2-bisthiazole 4 carboxylate reacts with NBS (N-bromosuccinylimine) in carbon tetrachloride as a solvent to produce a bormide, which is treated with silver nitrate to produce an intermediate hydroxyl-substituted compound 4a. Then the intermediate 4a is treated by DAST (diethylaminosulfur trifluoride) to produce an intermediate fluorine-substituted compound 4b.

The above bromide is treated by DBU (1,8-diazabicyclo[5,4,0]-undec-7-ene) as a base to produce an intermediate olefin 4c, which is further converted into an epoxy compound after treated with m-CPBA. The epoxy ring of the epoxy compound is selectively opened by hydrogenation in the present of Pd—C to produce an intermediate hydroxyl-substituted compound 4d, which is treated by DAST to produce an intermediate fluorine-substituted compound 4e.

The intermediate olefin 4c is catalyzed by potassium osmate in a mixed solvent of isopropanol and water to produce an intermediate bishydroxyl compound 4f through bishydroxylation.

Also, the intermediate olefin 4c may react with selenium dioxide in dioxane as a solvent to produce an aldehyde intermediate, which is reduced by sodium borohydride to produce an intermediate hydroxyl compound 4g. The intermediate 4g is then treated by DAST to produce an intermediate fluorine-substituted compound 4h.

The intermediate hydroxyl substituted compound 4g also can be alkylated by halogenated hydrocarbon $R_5X$ (wherein $R_5$ is $C_1$-$C_6$ alkyl) in the presence of NaH to produce an intermediate alkoxyl-substituted compound 4i.

Scheme II
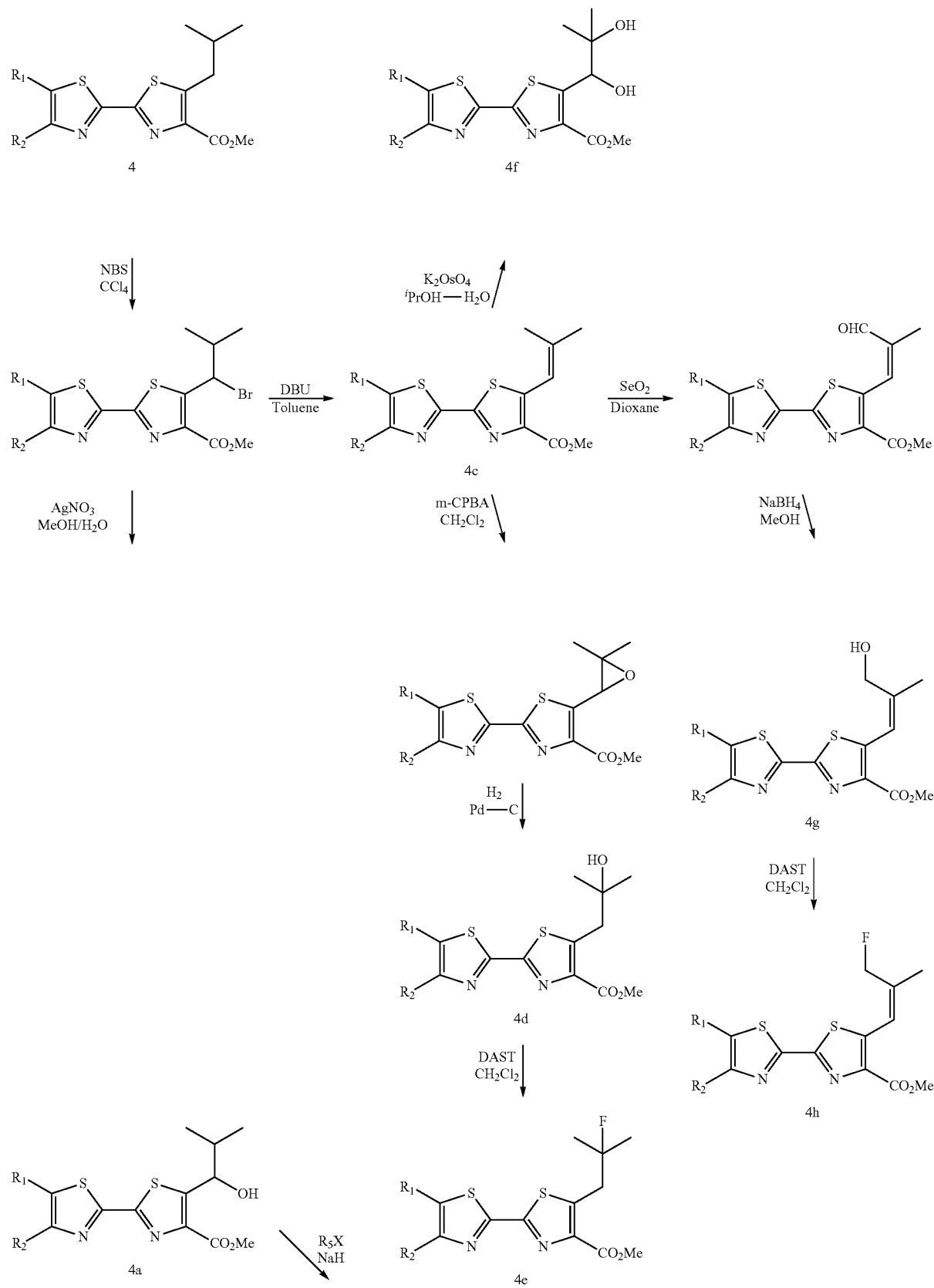

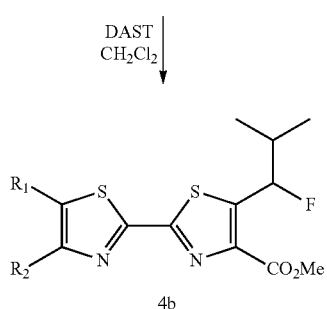
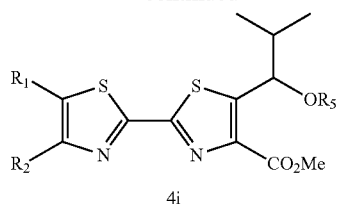
Staring from the intermediate 4, the 2',2-bisthiazole non-nucleoside compound of the present disclosure can be synthesized through the following procedures (schemes III, IV or V):
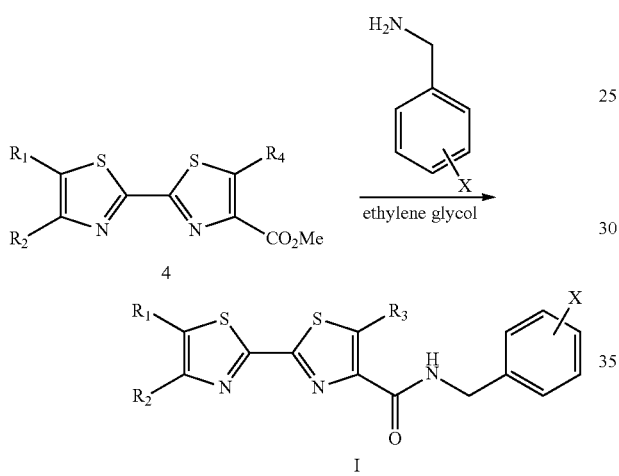
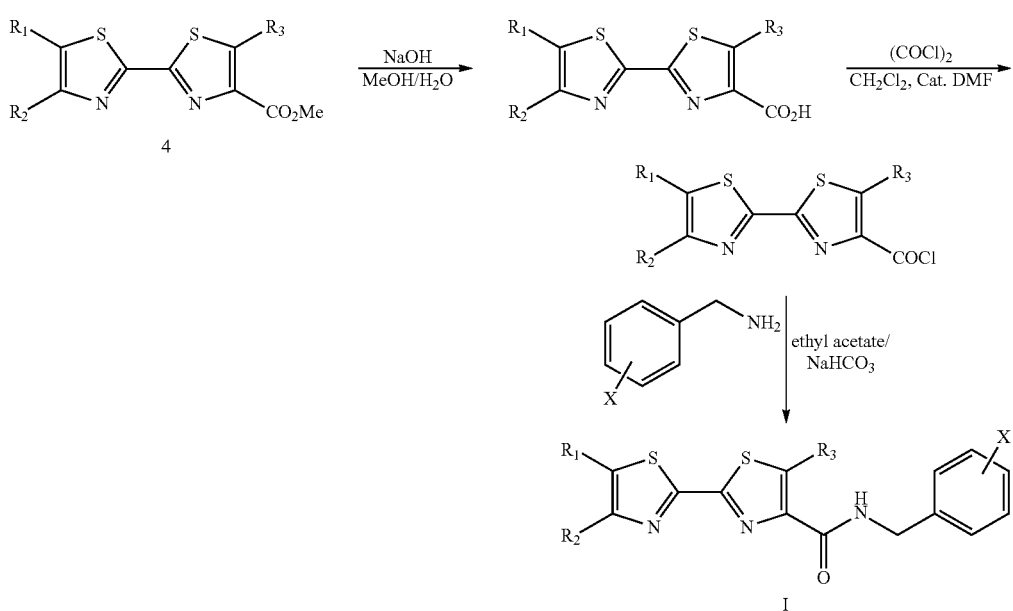

Scheme V

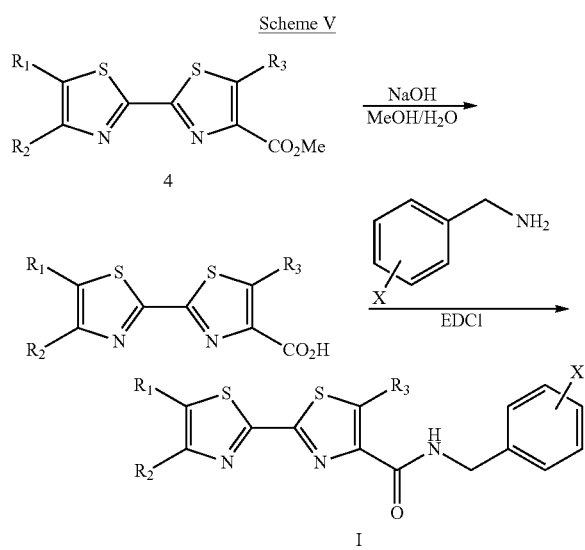

wherein, the definitions of $R_1$, $R_2$, $R_3$ and X in schemes III, IV and V are the same as above.

Particularly, the intermediate methyl 2',2-bisthiazolecarboxylate 4 can directly react with halogenated benzylamine as a nucleophilic reagent in a solvent of ethylene glycol at an elevated temperature to produce the 2',2-bisthiazole non-nucleoside compound of the present disclosure.

Alternatively, the intermediate methyl 2',2-bisthiazolecarboxylate 4 can be converted through hydrolyzation into a corresponding acid, which then reacts with oxalylchloride to produce an acyl chloride, and the acyl chloride then reacts with a halogenated benzylamine to produce the class of 2',2-bisthiazole heterocyclic compounds of the present disclosure.

Alternatively, the intermediate methyl 2',2-bisthiazolecarboxylate 4 can be converted through hydrolyzation into a corresponding acid, which reacts with a halogenated benzylamine in the presence of a condensing agent such as EDCI (1-ethyl-(3-dimethylaminopropyl) carbodiimide hydrochloride) to produce the class of 2',2-bisthiazole heterocyclic compounds of the present disclosure.

The novel class of 2',2-bisthiazole non-nucleoside heterocyclic compound provided by the present disclosure exhibits activities against both HBV and HCV, and thus can be used in treatment of hepatitis B and hepatitis C. Pharmacokinetic tests reveal that those compounds have good bioavailability and thus can be used to prepare drugs for treating hepatitis B and/or hepatitis C The present disclosure provides a method for treating hepatitis B or hepatitis C, comprising administrating a therapeutically effective amount of the 2',2-bisthiazole non-nucleoside compound of the present disclosure to a subject suffering from hepatitis B or hepatitis C.

The present disclosure further provides a pharmaceutical composition against viral hepatitis B and/or viral hepatitis C, which comprises a therapeutically effective amount of one or more of the 2',2-bisthiazole non-nucleoside compounds of the present disclosure as an active component, and may further comprise pharmaceutically acceptable adjuvants, such as a dispersant, an excipient, a disintegrant, an antioxidant, a sweetening agent, a coating agent, etc. The composition can be prepared by a conventional method in the field of pharmacy, and can be formulated into various routine dosage forms, such as tablet, coating tablet, capsule, powder, etc.

ADVANTAGEOUS EFFECT

The present invention designs and synthesizes a novel class of 2',2-bisthiazole non-nucleoside compounds, which can effectively inhibit the replication of HBV and HCV and thus can be used in treatment of viral hepatitis B and/or viral hepatitis C. Compared with the similar compounds disclosed previously in International Application No. PCT/CN2007/001861 (International Publication No. WO 2007/147336) by the present inventors, the novel 2',2-bisthiazole non-nucleoside compound of the present disclosure exhibits an anti-HCV activity while maintaining the anti-HBV activity, and overcomes the defect of low bioavailability of the previous compounds due to the incorporation of a polar group, such as double bond, hydroxyl, alkoxyl, halogen atom, etc., on the side chain, and thus possesses a good prospect of development.

BEST MODE FOR CARRYING OUT THE INVENTION

The invention will be described in detail in connection with the specific examples. However, the present invention is not limited to these examples.

PREPARATION EXAMPLES

In the following examples, NMR spectra were obtained on a Mercury-Vx 300M spectrometer from Varian. NMR calibration: δ H 7.26 ppm (CDCl₃). Mass spectra were obtained on a Agilent 1200 Quadrupole LC/MS instrument. Most reagents were provided by Shanghai Chemical Company. The silica gel plate (Model: HSGF 254) for thin-layer chromatography were produced by Huiyou silica development company, Yantai, Shandong. The silica gel (Model: zcx-11, 200-300 mesh) used in the normal phase column chromatography for purifying the compounds was produced by branch of Qingdao haiyang chemical plant.

Preparation Example 1

Synthesis of Intermediate Methyl 2',2-bisthiazole-4-carboxylates (1) Methyl 5-isobutyl-2',2-bisthiazole-4-carboxylate

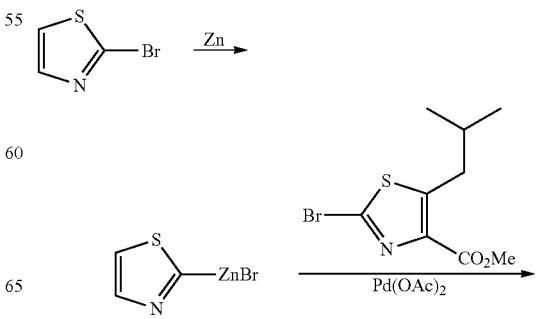

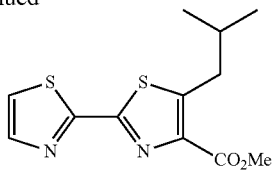

An activated Zn powder (84 g) was added into a 2 L three-necked bottle, and a fresh THF (600 ml) was added thereinto. When the mixture was heated to a inside temperature of about 60° C., a solution of 2-bromothiazole (200 g) in anhydrous THF (60 ml) was dropwise added over about 3-4 hours. The reaction was continued under reflux. The resultant zinc reagent was transferred into a solution of methyl 2-bromo-5-isobutylthiazole-4-carboxylate (233 g), palladium acetate (9.4 g) and triphenylphosphine (22 g) in anhydrous toluene solution (1.2 L), and heated to 80-85° C. and kept at this temperature for 1-1.5 hours. After cooling to room temperature, a 5% HCl aqueous solution (2 L) was added into the reaction mixture to separate the organic phase, and the aqueous phase was extracted with ethyl acetate. The combined organic phase was washed with a 5% HCl aqueous solution, and concentrated to obtain a brown-black oil, which was recrystallized in methanol to obtain methyl 5-isobutyl-2',2-bisthiazole-4-carboxylate as a yellowish solid (162 g). Molar yield: 69%.

$^1$H NMR (CDCl$_3$): δ 1.00 (s, 3H), 1.02 (s, 3H), 2.03 (m, 1H), 3.17-3.19 (d, J=7.2 Hz, 2H), 3.96 (s, 3H), 7.46-7.47 (d, J=3.3 Hz, 1H), 7.87-7.88 (d, J=3.3 Hz, 1H).

ESI-MS (m/z): 305.1 (M+Na)$^+$ (Calculated for C$_{12}$H$_{14}$N$_2$NaO$_2$S$_2$: 305.04).

(2) Methyl 5-(1-bromo-2-methylpropyl)-2',2-bisthiazole-4-carboxylate

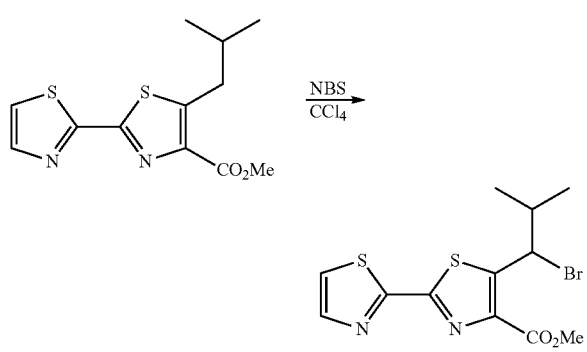

Methyl 5-isobutyl-2',2-bisthiazole-4-carboxylate (2.2 g) was dissolved in a mixture of carbon tetrachloride (60 ml) and dichloromethane (20 ml). After addition of NBS (N-bromosuccinimide, 1.8 g) and AIBN (2,2-azobisisobutyronitrile, 0.2 g), the resultant mixture was heated to reflux for 3 hours. The completion of the reaction was confirmed by TLC. The residue resulted from concentration was diluted with ethyl acetate. The organic phase was washed with water, dried and concentrated. The residue was purified by column chromatography to obtain methyl 5-(1-bromo-2-methylpropyl)-2',2-bisthiazole-4-carboxylate (2.8 g) as yellowish solid with an almost quantitative yield.

$^1$H NMR (300 MHz, CDCl$_3$): δ 1.03 (d, J=6.6 Hz, 3H), 1.23 (d, J=6.6 Hz, 3H), 2.24 (m, 1H), 3.98 (s, 3H), 6.11 (d, J=7.2 Hz, 1H), 7.51 (d, J=3.3 Hz, 1H), 7.90 (d, J=3.3 Hz, 1H).

(3) Methyl 5-(1-hydroxy-2-methylpropyl)-2',2-bisthiazole-4-carboxylate

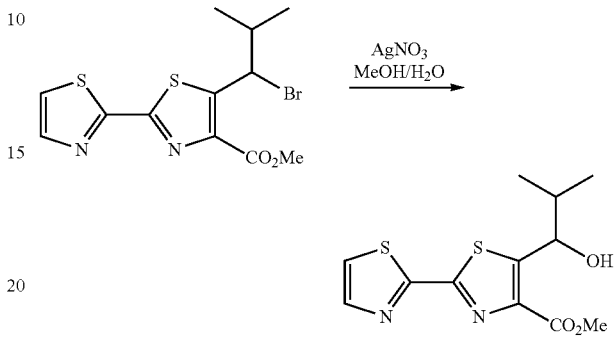

Methyl 5-(1-bromo-2-methylpropyl)-2',2-bisthiazole-4-carboxylate (235 mg) was dissolved in methanol (7 ml), and water (3 ml) and AgNO$_3$ (435 mg) was added thereinto. The reaction was performed at room temperature for 48 hours. TLC detection revealed that most of raw materials had been substantially depleted. The reaction mixture was filtered. The residue resulted from concentration of the filtrate was diluted with water, and fully extracted with ethyl acetate. The combined organic phase was concentrated and the resulted crude product was purified through column chromatography to obtain methyl 5-(1-hydroxy-2-methylpropyl)-2',2-bisthiazole-4-carboxylate (81 mg) as a nearly white solid. Molar yield: 42%.

$^1$H NMR (300 MHz, CDCl$_3$): δ 1.00 (d, J=6.6 Hz, 3H), 1.20 (d, J=6.6 Hz, 3H), 2.21 (m, 1H), 3.96 (s, 3H), 5.32 (t, J=5.4 Hz, 1H), 7.50 (d, J=3.3 Hz, 1H), 7.90 (d, J=3.3 Hz, 1H).

(4) Methyl 5-[1-(2-methylpropenyl)-2',2-bisthiazole-4-carboxylate

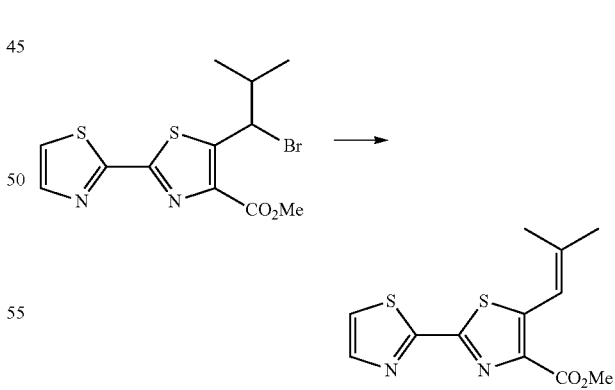

Methyl 5-(1-bromo-2-methylpropyl)-2',2-bisthiazole-4-carboxylate (1.2 g) was dissolved in toluene (50 ml), and DBU (1,8-diazabicyclo[5,4,0]undec-7-ene, 1.5 g) was added thereinto. The mixture was heated to reflux for 3 hours. The completion of the reaction was confirmed by TLC. The reaction mixture was diluted with ethyl acetate, washed with water, 5% HCl aqueous solution and saturated saline, respectively. The residue resulted from drying and concentrating was purified by column chromatography to obtain methyl 5-[1-(2-methylpropenyl)-2',2-bisthiazole-4-carboxylate (0.73 g) as a yellowish solid. Molar yield: 79%.

$^1$H NMR (300 MHz, CDCl$_3$): δ 2.06 (s, 6H), 3.98 (s, 3H), 7.31 (t, J=1.2 Hz, 1H), 7.47 (d, J=3.0 Hz, 1H), 7.89 (d, J=3.3 Hz, 1H).

(5) Methyl 5-[2-(3,3-dimethyl oxiranyl)]-2',2-bisthiazole-4-carboxylate

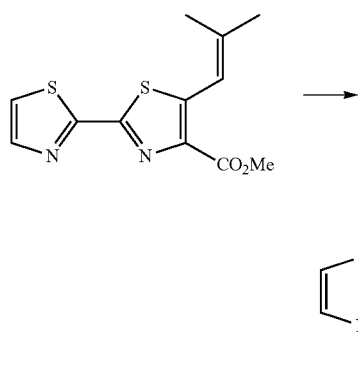

Methyl 5-[1-(2-methylpropenyl)]-2',2-bisthiazole-4-carboxylate (426 mg) was dissolved in chloroform (25 ml), and m-CPBA (metachloroperbenzoic acid, 600 mg) was added thereinto. The reaction was performed at room temperature for 3 hours. The completion of the reaction was confirmed by TLC. The reaction mixture was washed with saturated sodium bicarbonate aqueous solution and saturated sodium bisulfite aqueous solution, respectively. The organic phase was separated, dried and concentrated. The resultant crude product was purified by column chromatography to obtain methyl 542-(3,3-dimethyloxiranyl)]-2',2-bisthiazole-4-carboxylate (300 mg) as a white crystalline powder. Molar yield: 67%.

$^1$H NMR (300 MHz, CDCl$_3$): δ 1.23 (s, 3H), 1.56 (s, 3H), 3.99 (s, 3H), 4.42 (s, 1H), 7.48 (d, J =3.0 Hz, 1H), 7.89 (d, J=3.3 Hz, 1H).

(6) Methyl 5-(2-hydroxy-2-methylpropyl)-2',2-bisthiazole-4-carboxylate

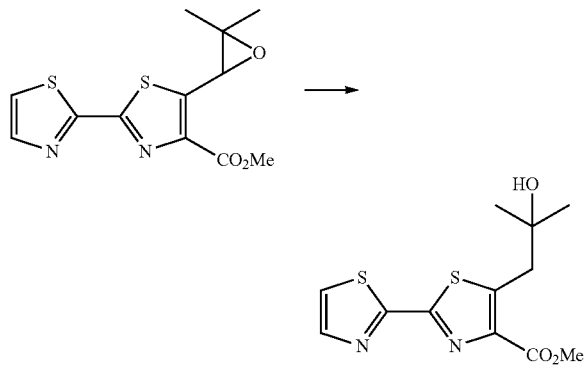

Methyl 5-[2-(3,3-dimethyloxiranyl)]-2',2-bisthiazole-4-carboxylate (200 mg) was dissolved in methanol (150 ml), and the catalyst Pd—C (10%, 10 mg) was added thereinto.

The hydrogen gas was bubbled into the mixture and fully replaced the air in the reactor. Then, the reaction was performed at room temperature for 5 hours. The completion of the reaction was confirmed by TLC. After unreacted hydrogen gas was replaced by nitrogen gas, the reaction mixture was filtered and the filtrate was concentrated. The residue was purified with column chromatography to obtain methyl 5-(2-hydroxy-2-methylpropyl)-2',2-bisthiazole-4-carboxylate (200 mg) as a nearly white solid with an almost quantitative yield.

$^1$H NMR (300 MHz, CDCl$_3$): δ 1.34 (s, 6H), 3.51 (s, 2H), 3.97 (s, 3H), 7.47 (d, J=3.0 Hz, 1H), 7.89 (d, J=3.0 Hz, 1H).

(7) Methyl 5-(1,2-dihydroxy-2-methylpropyl)-2',2-bisthiazole-4-carboxylate

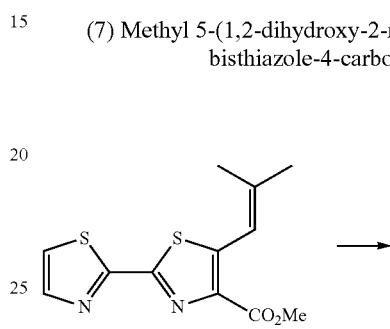

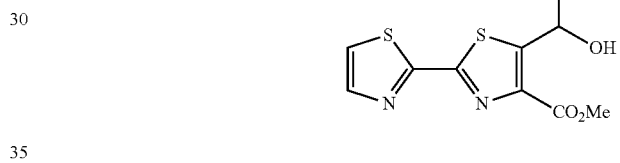

5-[1-(2-methylpropenyl)]-2',2-bisthiazole-4-carboxylate (500 mg) was dissolved in a mixed solvent of isopropyl alcohol (20 ml) and water (15 ml). Potassium osmate (25 mg) and N-methyl morpholine-N-oxide (NMO, 50%) (550 mg) were added thereinto. The reaction was performed over night at room temperature. On the next day, the completion of the reaction was confirmed by TLC. The reaction mixture was quenched with saturated sodium bisulfite aqueous solution, and extracted with ethyl acetate. The combined organic phase was washed with saturated saline, dried, filtered and concentrated to obtain methyl 5-(1,2-dihydroxy-2-methylpropyl)-2', 2-bisthiazole-4-carboxylate (494 mg) as a light brown oil. Molar yield: 87%.

$^1$H NMR (300 MHz, CDCl$_3$): δ 1.21 (s, 3H), 1.53 (s, 3H), 3.89 (s, 3H), 4.32 (s, 1H), 7.49 (d, J=3.0 Hz, 1H), 7.89 (d, J=3.3 Hz, 1H).

(8) Methyl 5-[1-(2-formylpropenyl)-2',2-bisthiazole-4-carboxylate

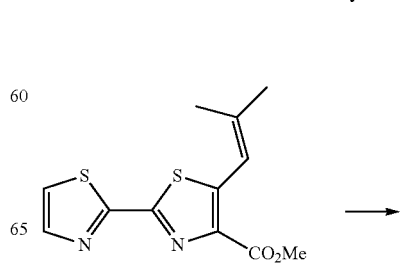

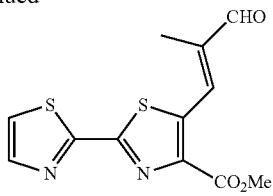

Methyl 5-[1-(2-methylpropenyl)]-2',2-bisthiazole-4-carboxylate (50 mg) was dissolved in dioxane (5 ml), and selenium oxide (30 mg) was added thereinto. The mixture was heated to reflux for 3 hours. TLC detection revealed that the raw materials had been substantially depleted. The reaction mixture was concentrated, and the solution of the residue dissolved in dichloromethane was transferred into a silica gel column (eluted with petroleum ether/ethyl acetate=5/1 (v/v)) for purification to obtain methyl 5-[1-(2-formylpropenyl)]-2',2-bisthiazole-4-carboxylate (31 mg) as a yellow solid. Molar yield: 60%.

$^1$H NMR (300 MHz, CDCl$_3$): δ 2.10 (s, 3H), 3.97 (s, 3H), 7.57 (d, J=3.0 Hz, 1H), 7.96 (d, J=3.0 Hz, 1H), 8.49 (d, J=1.5 Hz, 1H), 9.69 (s, 1H).

(9) Methyl 5-(3-hydroxy-2-methylpropyl)-2',2-bisthiazole-4-carboxylate

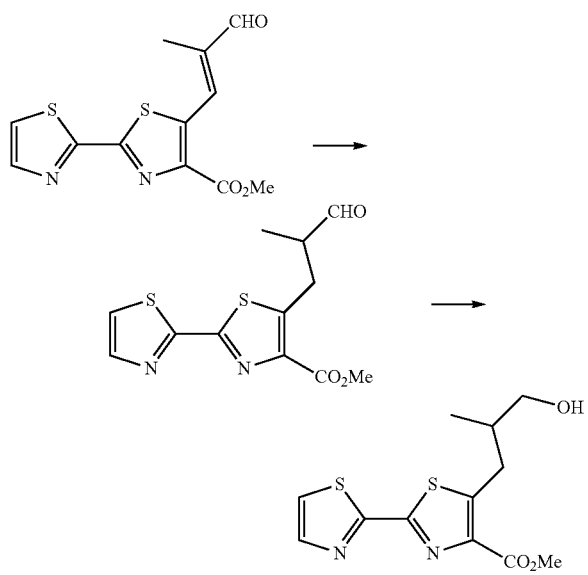

Methyl 5-[1-(2-formylpropenyl)]-2',2-bisthiazole-4-carboxylate (122 mg) was added into a mixed solvent of methanol (80 ml) and DMF (10 ml), and catalyst Pd—C (10%, 10 mg) was added thereinto. The air in the reactor was fully replaced by hydrogen gas, and the reaction was performed overnight. On the next day, the completion of the reaction was confirmed by TLC. The unreacted hydrogen gas was replaced by nitrogen gas, and the reaction mixture was filtered. The filtrate was concentrated and the residue was diluted with ethyl acetate, washed with water for three times and then with saturated saline. The organic phase was dried, filtered and concentrated to obtain methyl 5-(2-formylpropyl)-2',2-bisthiazole-4-carboxylate (123 mg) as a nearly colorless oil with an almost quantitative yield.

The product (123 mg) prepared above was dissolved in methanol (25 ml) and sodium borohydride (300 mg) was added thereinto under an ice bath. After reaction was performed at the same temperature for 15 min, the ice bath was removed. And the reaction was performed at room temperature for 3 hours. The completion of the reaction was confirmed by TLC. The reaction mixture was concentrated, and the residue was diluted with water and fully extracted with ethyl acetate. The combined organic phase was washed with saturated saline, dried, filtered and concentrated to obtain methyl 5-(3-hydroxy-2-methylpropyl)-2',2-bisthiazole-4-carboxylate (32 mg) as a nearly colorless oil. Molar yield: 26%. The crude product was directly used in the subsequent reaction without purification.

(10) Methyl 5-[1-(3-hydroxy-2-methylpropenyl)]-2',2-bisthiazole-4-carboxylate

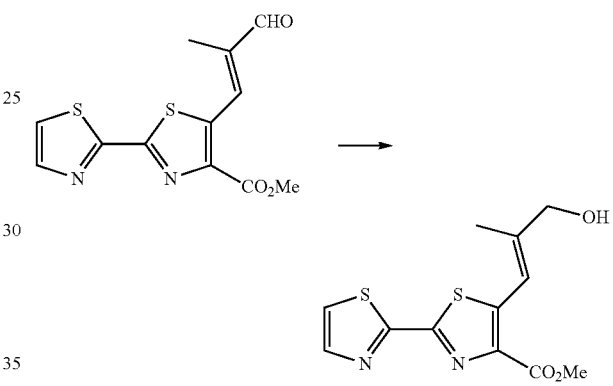

Methyl 5-[1-(2-formylpropenyl)]-2',2-bisthiazole-4-carboxylate (300 mg) was dissolved in methanol (300 ml). Sodium borohydride (200 mg) was added thereinto under an ice bath. After reaction was performed at the same temperature for 15 min, the ice bath was removed. The reaction was performed at room temperature for 1.5 hours. The completion of the reaction was confirmed by TLC. The reaction mixture was concentrated, and the residue was diluted with water and fully extracted with ethyl acetate. The combined organic phase was washed with saturated saline, dried, filtered and concentrated to obtain methyl 5-[1-(3-hydroxy-2-methylpropenyl)]-2',2-bisthiazole-4-carboxylate (198 mg) as a yellowish oil. Molar yield: 66%. The crude product was directly used in the subsequent reaction without purification.

(11) Methyl 5-(2-fluoro-2-methylpropyl)-2',2-bisthiazole-4-carboxylate

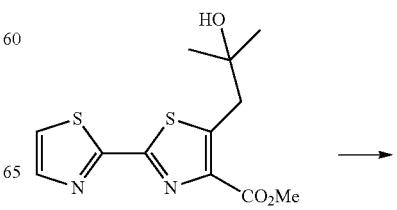

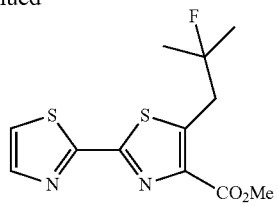

Methyl 5-(2-hydroxy-2-methylpropyl)-2',2-bisthiazole-4-carboxylate (63 mg) was dissolved in dichloromethane (5 ml). Diethylaminosulfur trifluoride (DAST, 0.1 ml) was dropwise added into the above solution under an ice bath. The reaction was performed at the temperature for 1 hour. The completion of the reaction was confirmed by TLC. The reaction was quenched with saturated sodium bicarbonate aqueous solution and extracted with ethyl acetate. The combined organic phase was dried, filtered and concentrated, and the residue was purified by column chromatography to obtain methyl 5-(2-fluoro-2-methylpropyl)-2',2-bisthiazole-4-carboxylate (20 mg) as a yellowish solid. Molar yield: 33%.

¹H NMR (300 MHz, CDCl₃): δ 1.39 (s, 3H), 1.46 (s, 3H), 3.69-3.77 (d, J=23.1 Hz, 1H), 3.97 (s, 3H), 7.47 (d, J=3.0 Hz, 1H), 7.90 (d, J=3.0 Hz, 1H).

(12) Methyl 5-(1-fluoro-2-methylpropyl)-2',2-bisthiazole-4-carboxylate

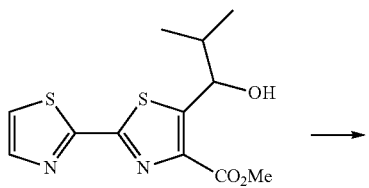

Methyl 5-(1-hydroxy-2-methylpropyl)-2',2-bisthiazole-4-carboxylate was used as a raw material to prepare methyl 5-(1-fluoro-2-methylpropyl)-2',2-bisthiazole-4-carboxylate following the method described in preparation example 1(11). Molar yield: 42%.

¹H NMR (300 MHz, CDCl₃): δ 1.07 (d, J=6.9 Hz, 6H), 2.24 (m, 1H), 3.99 (s, 3H), 6.21-6.39 (2d, J=5.4, 17.1 Hz, 1H), 7.51 (d, J=3.0 Hz, 1H), 7.92 (d, J=3.3 Hz, 1H).

ESI-MS (m/z): 323.1 (M+Na)⁺ (Calculated for $C_{12}H_{13}FN_2NaO_2S_2$: 323.03).

(13) Methyl 5-[1-(3-fluoro-2-methylpropenyl)-2',2-bisthiazole-4-carboxylate

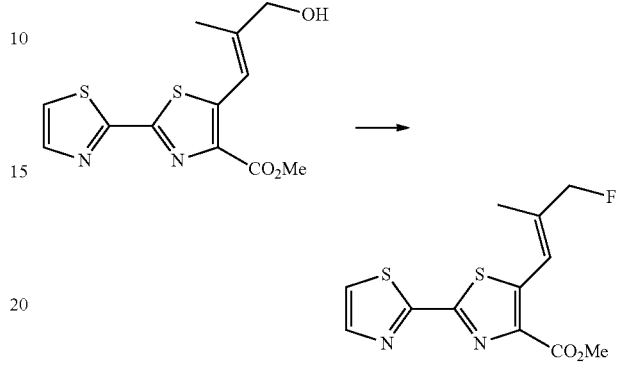

Methyl 5-[1-(3-hydroxy-2-methylpropenyl)]-2',2-bisthiazole-4-carboxylate was used as a raw material to prepare methyl 5-(1-fluoro-2-methylpropenyl)-2',2-bisthiazole-4-carboxylate following the method described in preparation example 1(11). Molar yield: 83%.

¹H NMR (300 MHz, CDCl₃): δ 2.07 (s, 3H), 2.24 (m, 1H), 3.97 (s, 3H), 4.89-5.05 (d, J=46.8 Hz, 1H), 7.51 (d, J=3.0 Hz, 1H), 7.61 (s, 1H), 7.92 (d, J=3.3 Hz, 1H).

ESI-MS (m/z): 321.0 (M+Na)⁺ (Calculated for $C_{12}H_{11}FN_2NaO_2S_2$: 321.01).

(14) Methyl 5-(1-methoxy-2-methylpropyl)-2',2-bisthiazole-4-carboxylate

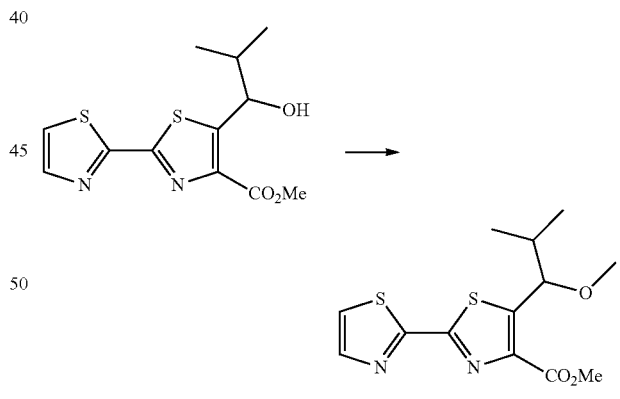

Methyl 5-(1-hydroxy-2-methylpropyl)-2',2-bisthiazole-4-carboxylate (55 mg) and iodomethane (0.3 ml) were dissolved in DMF (10 ml). NaH (60%, 50 mg) was added into the above solution under an ice bath. The mixture was warmed naturally and reacted for 6 hour. The completion of the reaction was confirmed by TLC. The reaction mixture was quenched with saturated ammonium chloride aqueous solution and extracted with ethyl acetate. The combined organic phase was washed with water and saturated saline, respectively. The organic phase was dried with anhydrous magnesium sulfate, filtered and concentrated. The resultant crude product was purified by column chromatography to obtain methyl 5-(1-methoxy-2-methylpropyl)-2',2-bisthiazole-4-carboxylate (52 mg) as a colorless oil. Molar yield: 86%.

$^1$H NMR (300 MHz, CDCl$_3$): δ 0.95 (d, J=6.6 Hz, 3H), 1.02 (d, J=6.6 Hz, 3H), 2.05 (m, 1H), 3.40 (s, 3H), 3.98 (s, 3H), 5.07 (d, J=6.0 Hz, 1H), 7.49 (d, J=3.0 Hz, 1H), 7.91 (d, J=3.0 Hz, 1H).

(15) Isopropyl 5'-methyl-5-isobutyl-2',2-bisthiazole-4-carboxylate

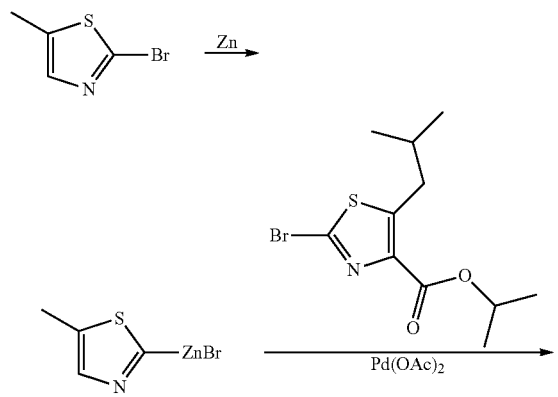

2-bromo-5-methylthiazole and isopropyl 2-bromo-5-isobutylthiazole-4-carboxylate were used as raw materials to obtain isopropyl 5'-methyl-5-isobutyl-2',2-bisthiazole-4-carboxylate as a yellowish solid following the method described in preparation example 1(1). Molar yield: 66%.

$^1$H NMR (300 MHz, CDCl$_3$): δ 0.99 (d, J=6.6 Hz, 6H), 1.41 (d, J=6.3 Hz, 6H), 1.98 (m, 1H), 2.53 (s, 3H), 3.10 (d, J=7.2 Hz, 2H), 5.28 (m, 1H), 7.51 (s, 1H).

(16) isopropyl 5'-methyl-5-(1-bromo-2-methylpropyl)-2',2-bisthiazole-4-carboxylate

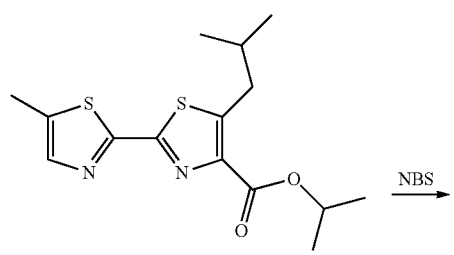

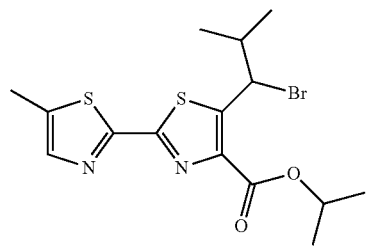

Isopropyl 5'-methyl-5-isobutyl-2',2-bisthiazole-4-carboxylate was used as a raw material to obtain isopropyl 5'-methyl-5-(1-bromo-2-methylpropyl)-2',2-bithiazole-4-carboxylate as a yellowish oil following the method described in preparation example 1(2) with an almost quantitative yield. The product was directly used in the subsequent reaction.

$^1$H NMR (300 MHz, CDCl$_3$): δ 0.92 (d, J=6.6 Hz, 3H), 1.20 (d, J=6.6 Hz, 3H), 1.44 (m, 6H), 2.24 (m, 1H), 2.54 (s, 3H), 5.28 (m, 1H), 6.04 (d, J=6.6 Hz, 3H), 7.54 (s, 1H).

(17) Isopropyl 5'-methyl-5-(1-hydroxy-2-methylpropyl)-2',2-bisthiazole-4-carboxylate

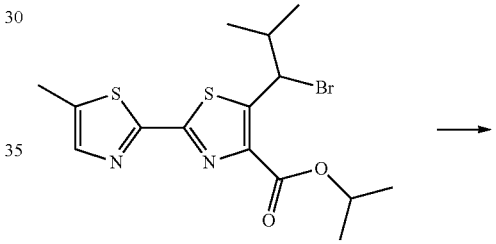

Isopropyl 5'-methyl-5-(1-bromo-2-methylpropyl)-2',2-bisthiazole-4-carboxylate was used as a raw material to obtain isopropyl 5'-methyl-5-(1-hydroxy-2-methylpropyl)-2',2-bithiazole-4-carboxylate as a yellowish solid following the method described in preparation example 1(3). Molar yield: 13%.

¹H NMR (300 MHz, CDCl₃): δ 0.97 (d, J=6.6 Hz, 3H), 1.05 (d, J=6.6 Hz, 3H), 1.44 (d, J=6.3 Hz, 6H), 2.10 (m, 1H), 2.54 (s, 3H), 3.28 (d, J=5.7 Hz, 1H), 5.26 (m, 1H), 7.53 (s, 1H).

(18) Isopropyl 5'-methyl-5-(1-fluoro-2-methylpropyl)-2',2-bisthiazole-4-carboxylate

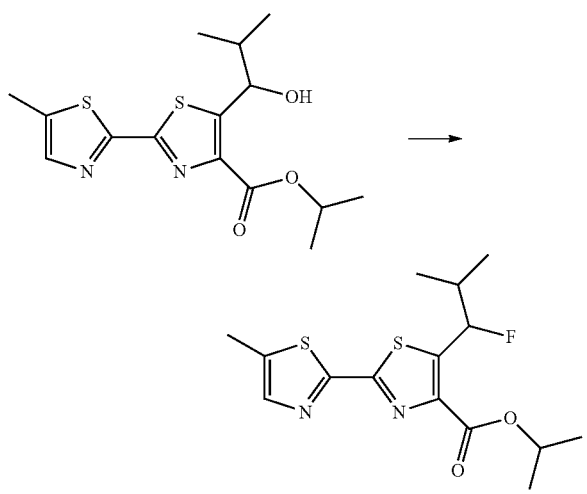

Isopropyl 5'-methyl-5-(1-fluoro-2-methylpropyl)-2',2-bisthiazole-4-carboxylate as a yellowish solid was prepared following the method described in preparation example 1(11) with a quantitative yield.

¹H NMR (300 MHz, CDCl₃): δ 1.04 (d, J=6.6 Hz, 6H), 1.25 (m, 6H), 2.20 (m, 1H), 2.55 (s, 3H), 5.28 (m, 1H), 6.15-6.33 (2d, J=5.4, 17.1 Hz, 1H), 7.55 (s, 1H).

(19) Isopropyl 5'-methyl-5-[1-(2-methylpropenyl)]-2',2-bisthiazole-4-carboxylate

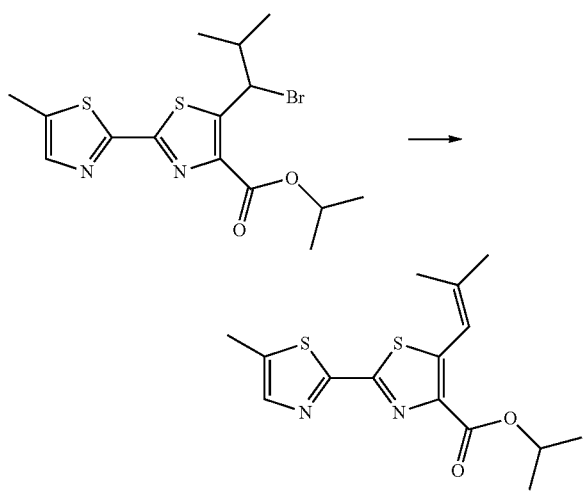

Isopropyl 5'-methyl-5-(1-bromo-2-methylpropyl)-2',2-bisthiazole-4-carboxylate was used as a raw material to obtain isopropyl 5'-methyl-5-[1-(2-methylpropenyl)]-2',2-bithiazole-4-carboxylate as a yellow solid following the method described in preparation example 1(4). Molar yield: 40%.

¹H NMR (300 MHz, CDCl₃): δ1.55 (s, 6H), 2.03 (s, 6H), 2.54 (s, 3H), 5.27 (m, 1H), 7.20 (s, 1H), 7.54 (s, 1H).

Preparation Example 2

The Synthesis of 2',2-dithiazole Non-Nucleoside Compounds (1) N-(p-fluorobenzyl)-5-(1-hydroxy-2-methylpropyl)-2',2-bisthiazole-4-formamide (391-1)

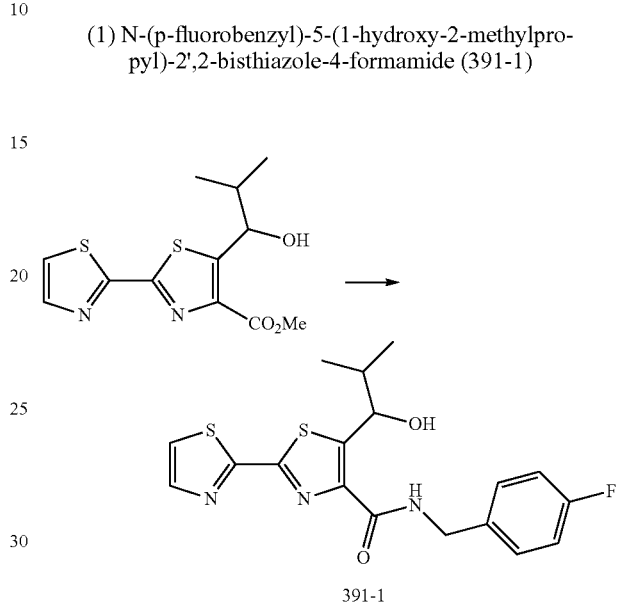

391-1

Methyl 5-(1-hydroxy-2-methylpropyl)-2',2-bisthiazole-4-carboxylate (300 mg) was dissolved in ethylene glycol (3 ml), and p-fluorobenzylamine (125 mg) was added thereinto. The reaction was performed under nitrogen atmosphere at 150° C. overnight. The completion of the reaction was confirmed by TLC. The reaction mixture was diluted with water and extracted with ethyl acetate. After the combined organic phase was washed with water, 5% HCl aqueous solution and saturated saline, respectively, it was dried and concentrated. The crude product was further purified by column chromatography to obtain N-(p-fluorobenzyl)-5-(1-hydroxy-2-methylpropyl)-2',2-bisthiazole-4-formamide (17 mg) as a yellowish oil. Molar yield: 50%.

¹H NMR (300 MHz, CDCl₃): δ 0.93 (d, J=6.6 Hz, 3H), 1.18 (d, J=6.6 Hz, 3H), 2.20 (m, 1H), 4.63 (d, J=6.0 Hz, 2H), 4.89 (t, J=7.8 Hz, 1H), 5.65 (d, J=8.4 Hz, 1H), 7.05 (m, 2H), 7.34 (m, 2H), 7.46 (d, J=3.0 Hz, 1H), 7.89 (d, J=3.0 Hz, 1H), 7.94 (m, 1H).

(2) N-(p-fluorobenzyl)-5-(2-hydroxy-2-methylpropyl)-2',2-bisthiazole-4-formamide (391-2)

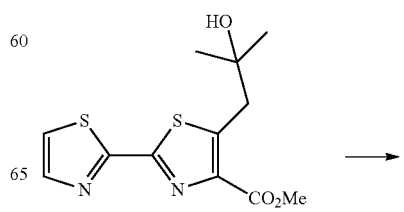

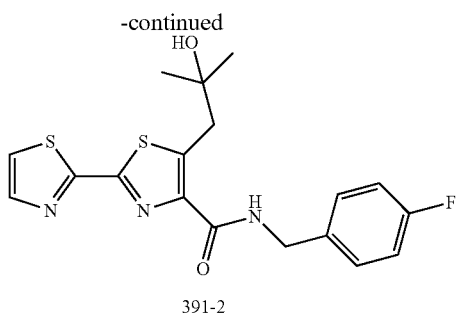

391-2

N-(p-fluorobenzyl)-5-(2-hydroxy-2-methylpropyl)-2',2-bisthiazole-4-formamide as a yellowish oil was prepared following the method described in preparation example 2(1). Molar yield: 55%.

¹H NMR (300 MHz, CDCl₃): δ 1.28 (s, 6H), 3.52 (s, 2H), 3.97 (s, 1H), 4.61 (d, J=6.0 Hz, 2H), 7.04 (m, 2H), 7.34 (m, 2H), 7.45 (d, J=3.0 Hz, 1H), 7.88 (d, J=3.0 Hz, 1H), 7.89 (s, 1H).

(3) N-(p-fluorobenzyl)-5-(3-hydroxy-2-methylpropyl)-2',2-bisthiazole-4-formamide (391-3)

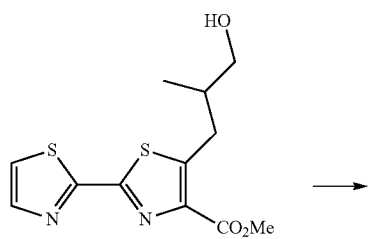

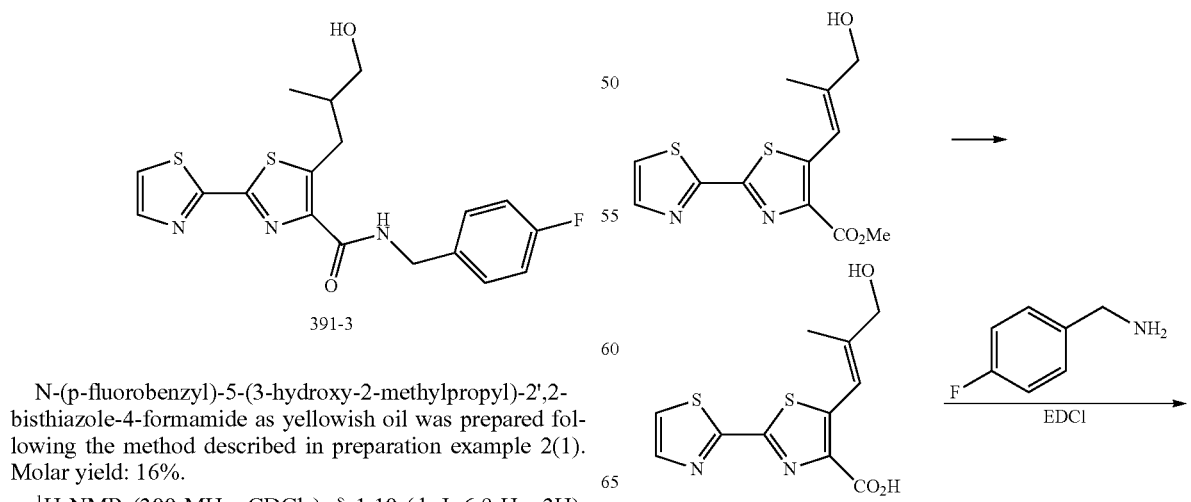

391-3

N-(p-fluorobenzyl)-5-(3-hydroxy-2-methylpropyl)-2',2-bisthiazole-4-formamide as yellowish oil was prepared following the method described in preparation example 2(1). Molar yield: 16%.

¹H NMR (300 MHz, CDCl₃): δ 1.10 (d, J=6.9 Hz, 3H), 2.04 (br s, 1H), 3.24 (dd, J=5.4, 14.4 Hz, 2H), 3.34 (m, 1H), 3.54 (m, 1H), 3.71 (dd, J=6.0, 14.1 Hz, 2H), 3.67 (m, 2H), 7.05 (m, 2H), 7.35 (m, 2H), 7.46 (d, J=3.3 Hz, 1H), 7.87 (s, 1H), 7.88 (d, J=3.3 Hz, 1H).

(4) N-(p-fluorobenzyl)-5-(1,2-dihydroxy-2-methylpropyl)-2',2-bisthiazole-4-formamide (407)

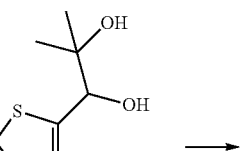

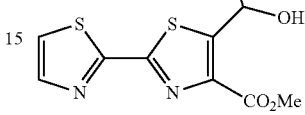

407

N-(p-fluorobenzyl)-5-(1,2-dihydroxy-2-methylpropyl)-2',2-bisthiazole-4-formamide as a yellowish oil was prepared following the method described in preparation example 2(1). Molar yield: 26%.

¹H NMR (300 MHz, CDCl₃): δ 1.32 (s, 6H), 4.61 (d, J=6.0 Hz, 1H), 5.69 (s, 1H), 7.07 (m, 2H), 7.37 (m, 2H), 7.45 (d, J=3.0 Hz, 1H), 7.89 (d, J=3.0 Hz, 1H), 7.90 (s, 1H).

(5) N-(p-fluorobenzyl)-5-[1-(3-hydroxy-2-methylpropenyl)]-2',2-bisthiazole-4-formamide (389)

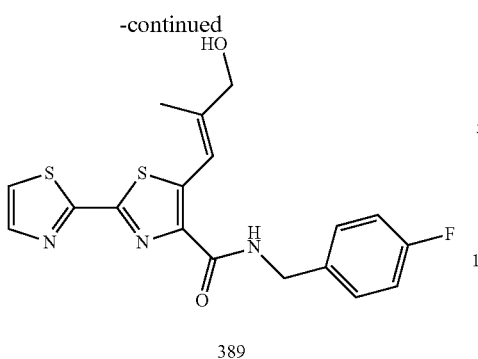

389

Methyl 5-[1-(3-hydroxy-2-methylpropenyl)]-2',2-bisthiazole-4-carboxylate (120 mg) was dissolved a mixed solvent of methanol (20 ml) and water (10 ml), and lithium hydroxide monohydrate (50 mg) was added thereinto. The reaction was performed at room temperature overnight. Once the reaction was completed, the mixture was concentrated under reduced pressure to remove most of methanol. The resultant water phase was adjusted to be acidic with 5% HCl aqueous solution to become opacity. The water phase was fully extracted by dichloromethane, and the obtained organic phase was dried with anhydrous magnesium sulfate, filtered and concentrated to obtain 5-[1-(3-hydroxy-2-methylpropenyl)]-2', 2-bisthiazole-4-carboxylic acid (110 mg) as a yellowish solid with an almost quantitative yield. The product was directly used in the subsequent reaction.

5-[1-(3-hydroxy-2-methylpropenyl)]-2',2-bisthiazole-4-carboxylic acid (62 mg) obtained from above was dissolved in DMF (N,N-dimethylformamide) (20 ml), and p-fluorobenzylamine (140 mg), EDCI (300 mg) and 4-dimethylaminopyridine (DMAP, 30 mg) were added thereinto. The reaction was performed at room temperature overnight. Once the reaction was completed, the reaction mixture was diluted with water and fully extracted with ethyl acetate. The resultant organic phase was washed with water, 5% HCl aqueous solution and saturated saline, respectively, dried with anhydrous magnesium sulfate, filtered and concentrated. The crude product was further purified by column chromatography (eluted by petroleum ether/acetone=4/1) to obtain N-(p-fluorobenzyl)-5-[1-(3-hydroxy-2-methylpropenyl)]-2',2-bisthiazole-4-formamide as a yellowish solid. Molar yield: 32%.

$^1$H NMR (300 MHz, CDCl$_3$): δ 2.05 (s, 3H), 4.28 (s, 2H), 4.62 (d, J=6.0 Hz, 2H), 7.04 (m, 2H), 7.38 (m, 2H), 7.48 (d, J=3.0 Hz, 1H), 7.83 (m, 1H), 7.89 (d, J=3.6 Hz, 1H), 7.93 (s, 1H).

ESI-MS (m/z): 412.0 (M+Na)$^+$ (Calculated for C$_{18}$H$_{16}$FN$_3$NaO$_2$S$_2$: 412.06).

(6) N-(p-fluorobenzyl)-5'-methyl-5-(1-hydroxy-2-methylpropyl)-2',2-bisthiazole-4-formamide (Me-391-1)

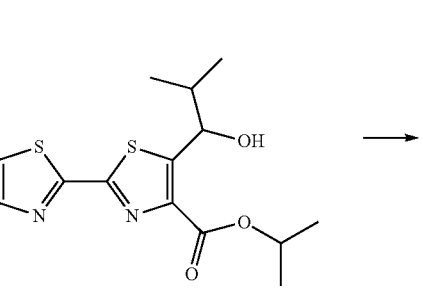

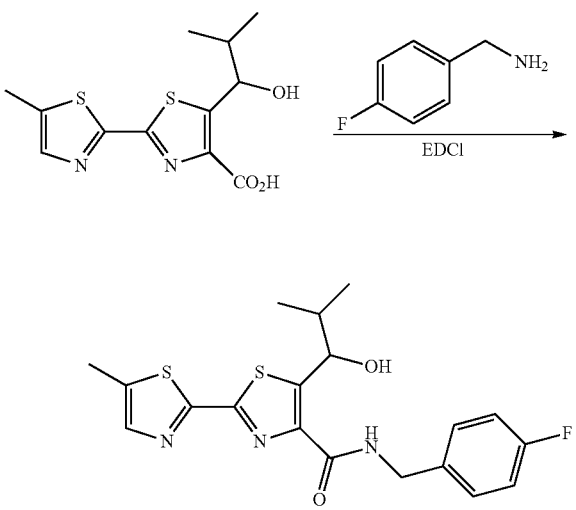

Me-391-1

Isopropyl 5'-methyl-5-(1-hydroxy-2-methylpropyl)-2',2-bisthiazole-4-carboxylate was used as a raw material through hydrolysis, condensation and column chromatography (petroleum ether/acetone=5/1) to obtain N-(p-fluorobenzyl)-5'-methyl-5-(1-hydroxy-2-methylpropyl)-2',2-bisthiazole-4-formamide as a colorless oil following the method described in preparation example 2(5). Molar yield: 43%.

$^1$H NMR (300 MHz, CDCl$_3$): δ 0.92 (d, J=6.6 Hz, 3H), 1.01 (d, J=6.6 Hz, 3H), 2.17 (m, 1H), 2.53 (s, 3H), 4.62 (d, J=6.0 Hz, 2H), 4.83 (t, J=7.8 Hz, 1H), 5.76 (d, J=8.4 Hz, 1H), 7.05 (m, 2H), 7.35 (m, 2H), 7.54 (s, 1H), 7.89 (d, J=3.6 Hz, 1H), 7.93 (m, 1H).

(7) N-(p-fluorobenzyl)-5-[1-(2-methylpropenyl)]-2', 2-bisthiazole-4-formamide (373)

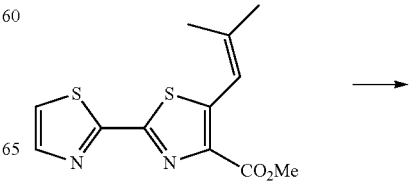

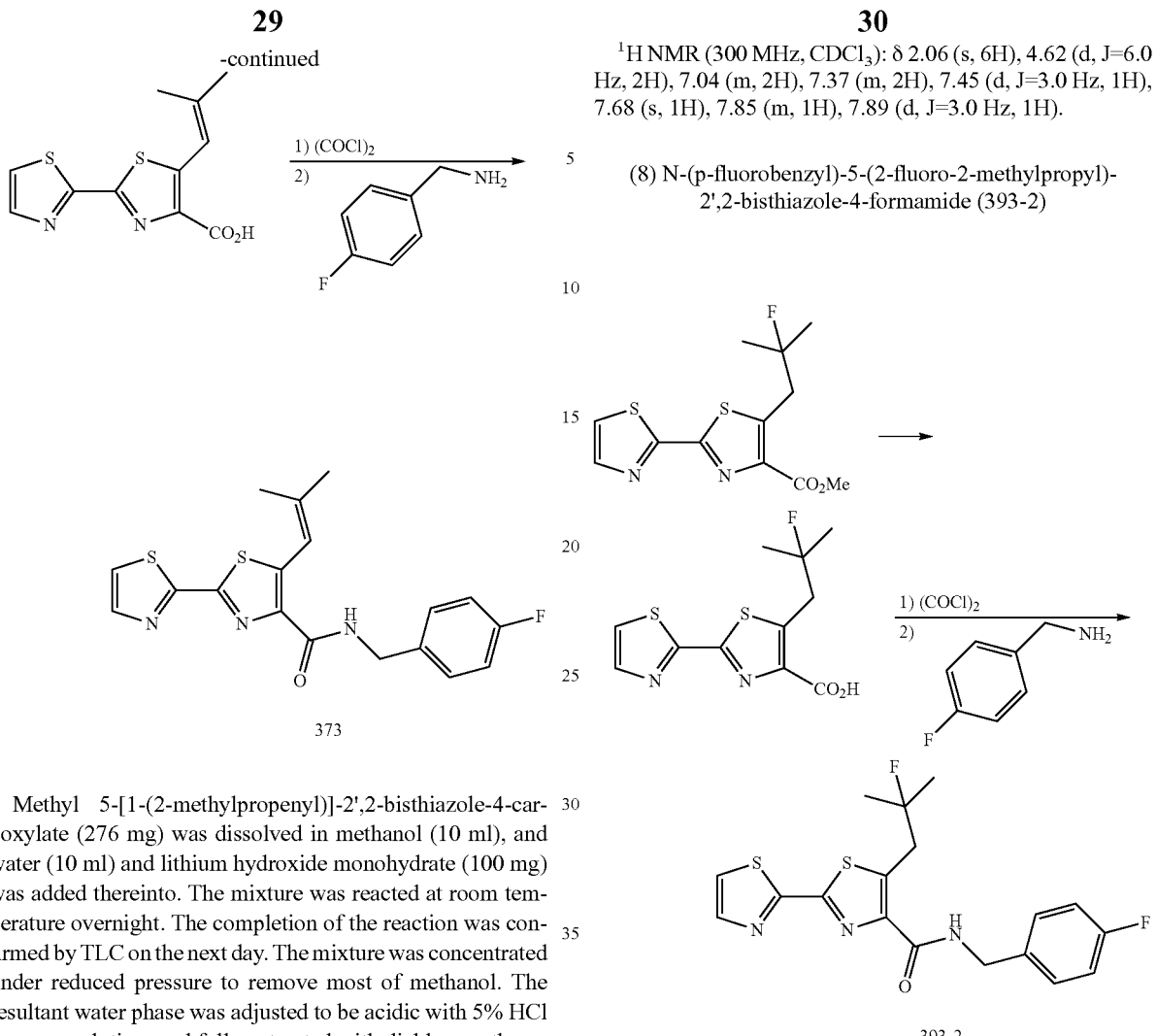

Methyl 5-[1-(2-methylpropenyl)]-2',2-bisthiazole-4-carboxylate (276 mg) was dissolved in methanol (10 ml), and water (10 ml) and lithium hydroxide monohydrate (100 mg) was added thereinto. The mixture was reacted at room temperature overnight. The completion of the reaction was confirmed by TLC on the next day. The mixture was concentrated under reduced pressure to remove most of methanol. The resultant water phase was adjusted to be acidic with 5% HCl aqueous solution, and fully extracted with dichloromethane. The combined organic phase was washed with water, dried, filtered and concentrated to obtain 5-[1-(2-methylpropenyl)]-2',2-bisthiazole-4-carboxylic acid as a yellowish solid (275 mg) with an almost quantitative yield. The product was used directly in the subsequent reaction.

The resultant 5-[1-(2-methylpropenyl)]-2',2-bisthiazole-4-carboxylic acid (257 mg) was dissolved in dichloromethane (15 ml), and one drop of DMF and oxalyl chloride (0.15 ml) were added thereinto. The reaction was performed at room temperature for 3 hours, and a yellowish solid was obtained after concentration. The solution formed by dissolving the solid obtained above in ethyl acetate (15 ml) was added dropwise into a mixture of a solution of p-fluorobenzylamine (180 mg) in ethyl acetate (15 ml) and a solution of sodium bicarbonate (200 mg) in water (10 ml) under an ice bath. This mixture was allowed to warm naturally to temperature and reacted overnight. The completion of the reaction was confirmed by TLC on the next day. The organic phase was separated, and the water phase was extracted by ethyl acetate. The combined organic phase was washed with 5% HCl aqueous solution and saturated saline, respectively, dried, filtered and concentrated. The residue was further purified by column chromatography to obtain N-(p-fluorobenzyl)-5-1-(2-methylpropenyl)]-2',2-bisthiazole-4-formamide (284 mg) as a yellow solid. Molar yield of two steps was 77%.

$^1$H NMR (300 MHz, CDCl$_3$): δ 2.06 (s, 6H), 4.62 (d, J=6.0 Hz, 2H), 7.04 (m, 2H), 7.37 (m, 2H), 7.45 (d, J=3.0 Hz, 1H), 7.68 (s, 1H), 7.85 (m, 1H), 7.89 (d, J=3.0 Hz, 1H).

(8) N-(p-fluorobenzyl)-5-(2-fluoro-2-methylpropyl)-2',2-bisthiazole-4-formamide (393-2)

N-(p-fluorobenzyl)-5-(2-fluoro-2-methylpropyl)-2',2-bisthiazole-4-formamide as a yellowish oil was prepared following the method described in preparation example 2(7) with a quantitative yield of two steps.

$^1$H NMR (300 MHz, CDCl$_3$): δ 1.40 (s, 3H), 1.47 (s, 3H), 3.90 (d, J=24.0 Hz, 2H), 4.60 (d, J=6.6 Hz, 2H), 7.07 (m, 2H), 7.34 (m, 2H), 7.44 (d, J=3.0 Hz, 1H), 7.87 (m, 1H), 7.89 (d, J=3.0 Hz, 1H).

ESI-MS (m/z): 416.1 (M+Na)$^+$ (Calculated for C$_{18}$H$_{17}$F$_2$N$_3$NaOS$_2$: 416.07).

(9) N-(p-fluorobenzyl)-5-(1-fluoro-2-methylpropyl)-2',2-bisthiazole-4-formamide (393-1)

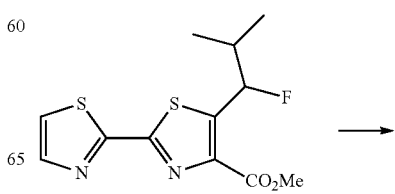

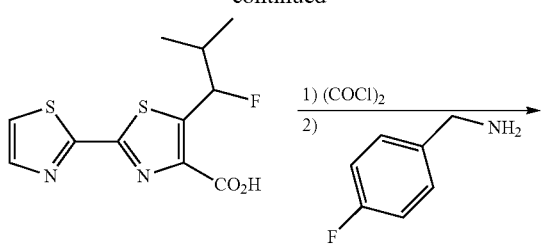

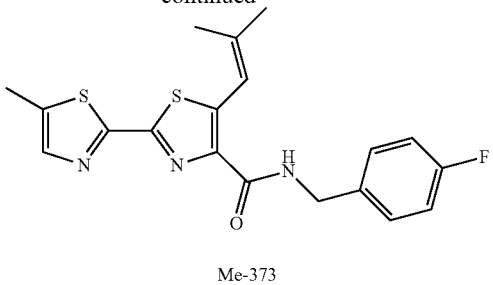

Me-373

N-(p-fluorobenzyl)-5'-methyl-5-[1-(2-methylpropenyl)]-2',2-bisthiazole-4-formamide as a yellowish solid was prepared following the method described in preparation example 2(7). Molar yield of two steps: 93%.

$^1$H NMR (300 MHz, CDCl$_3$): δ 2.04 (s, 6H), 2.53 (s, 3H), 4.62 (d, J=6.3 Hz, 2H), 7.04 (m, 2H), 7.35 (m, 2H), 7.53 (s, 1H), 7.66 (s, 1H), 7.84 (m, 1H).

(11) N-(p-fluorobenzyl)-5'-methyl-5-(1-fluoro-2-methylpropyl)-2',2-bisthiazole-4-formamide (Me-393-1)

393-1

N-(p-fluorobenzyl)-5-(1-fluoro-2-methylpropyl)-2',2-bisthiazole-4-formamide as a colorless oil was prepared following the method described in preparation example 2(7) with a quantitative yield.

$^1$H NMR (300 MHz, CDCl$_3$): δ 1.06 (t, J=6.6 Hz, 6H), 2.26 (m, 1H), 4.63 (m, 2H), 6.47-6.65 (2d, J=5.4, 46.5 Hz, 1H), 7.05 (m, 2H), 7.35 (m, 2H), 7.48 (d, J=3.0 Hz, 1H), 7.77 (m, 1H), 7.91 (d, J=3.0 Hz, 1H).

ESI-MS (m/z): 416.1 (M+Na)$^+$ (Calculated for C$_{18}$H$_{17}$F$_2$N$_3$NaOS$_2$: 416.07).

(10) N-(p-fluorobenzyl)-5'-methyl-5-[1-(2-methylpropenyl)]-2',2-bisthiazole-4-formamide (Me-373)

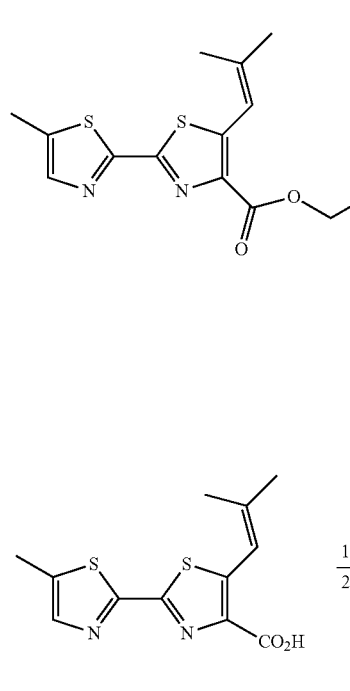

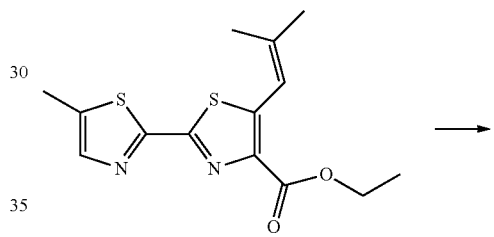

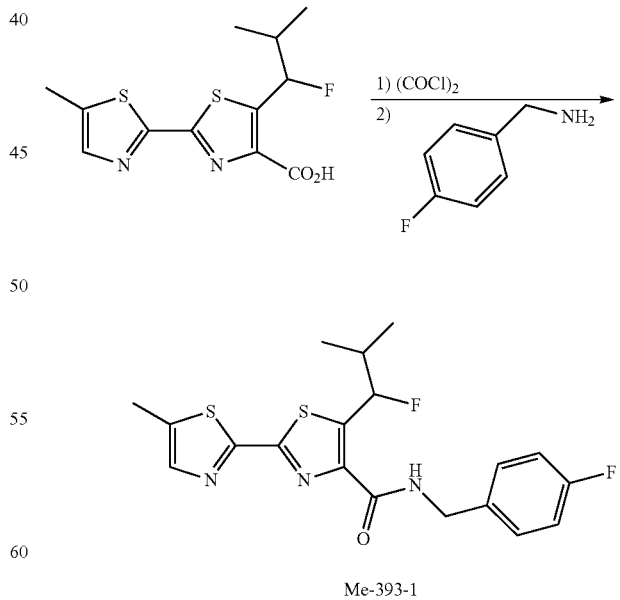

Me-393-1

N-(p-fluorobenzyl)-5'-methyl-5-(1-fluoro-2-methylpropyl)-2',2-bisthiazole-4-formamide as a nearly colorless oil was prepared following the method described in preparation example 2(7). Molar yield of two steps: 83%.

$^1$H NMR (300 MHz, CDCl$_3$): δ 1.05 (m, 6H), 2.25 (m, 1H), 2.54 (s, 3H), 4.61 (m, 2H), 6.46-6.64 (2d, J=5.4, 46.8 Hz, 1H), 7.05 (m, 2H), 7.33 (m, 2H), 7.55 (s, 1H), 7.76 (m, 1H).

(12) N-(p-fluorobenzyl)-5-[1-(2-fluoromethylpropenyl)]-2',2-bisthiazole-4-formamide (391-F)

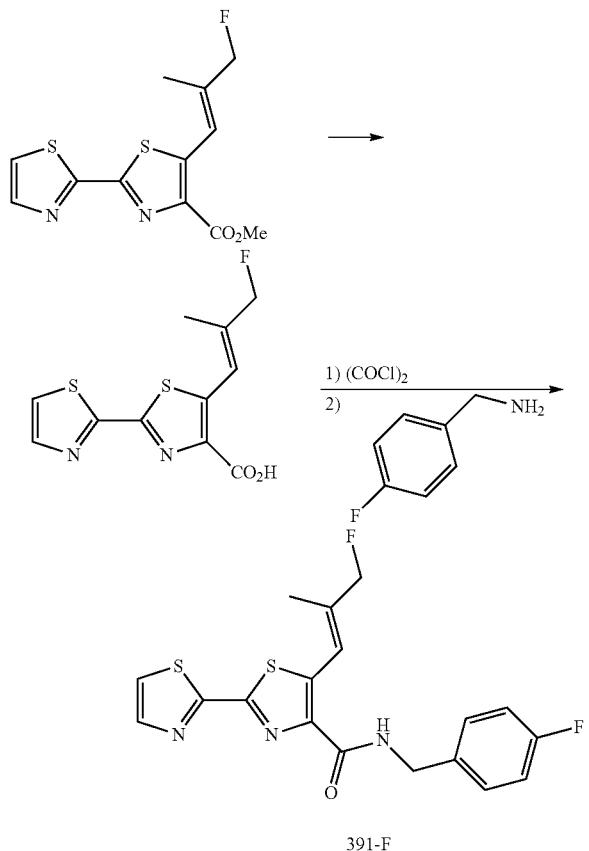

391-F

N-(p-fluorobenzyl)-5-[1-(2-fluoromethylpropenyl)]-2',2-bisthiazole-4-formamide as a nearly white solid was prepared following the method described in preparation example 2(7). Molar yield of two steps was 68%.

$^1$H NMR (300 MHz, CDCl$_3$): δ 2.09 (s, 3H), 4.63 (d, J=6.0 Hz, 2H), 4.89 (s, 1H), 5.05 (s, 1H), 7.05 (m, 2H), 7.36 (m, 2H), 7.50 (d, J=3.0 Hz, 1H), 7.88 (m, 1H), 7.92 (d, J=3.0 Hz, 1H), 8.00 (s, 1H).

ESI-MS (m/z): 414.0 (M+Na)$^+$ (Calculated for C$_{18}$H$_{15}$F$_2$N$_3$NaOS$_2$: 414.05).

(13) N-(p-fluorobenzyl)-5-(1-methoxy-2-methylpropyl)-2',2-bisthiazole-4-formamide (405-1)

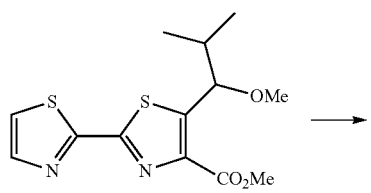

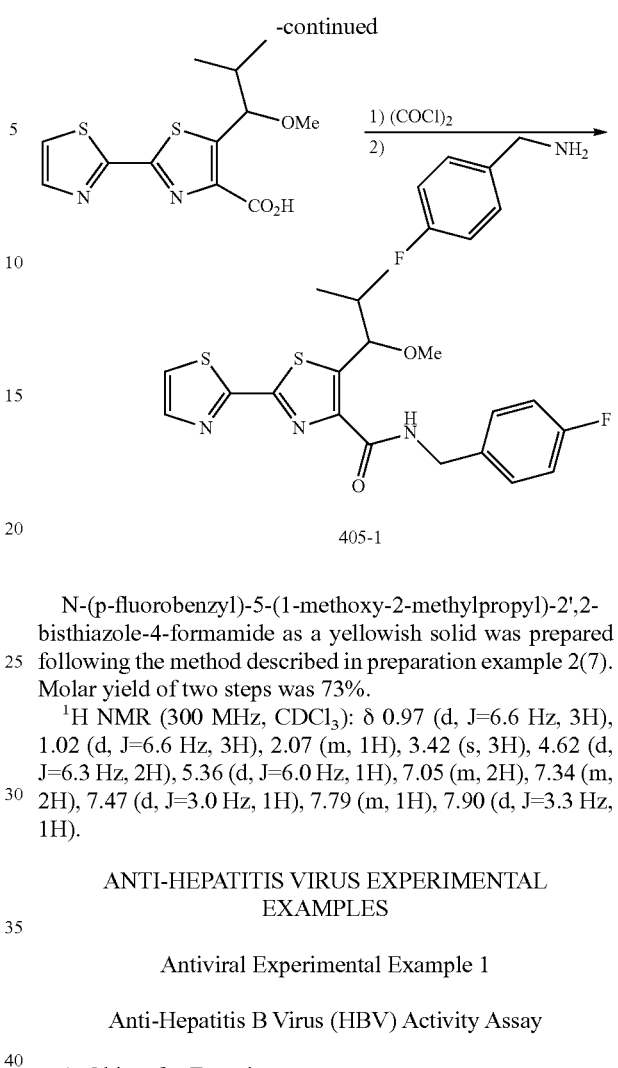

405-1

N-(p-fluorobenzyl)-5-(1-methoxy-2-methylpropyl)-2',2-bisthiazole-4-formamide as a yellowish solid was prepared following the method described in preparation example 2(7). Molar yield of two steps was 73%.

$^1$H NMR (300 MHz, CDCl$_3$): δ 0.97 (d, J=6.6 Hz, 3H), 1.02 (d, J=6.6 Hz, 3H), 2.07 (m, 1H), 3.42 (s, 3H), 4.62 (d, J=6.3 Hz, 2H), 5.36 (d, J=6.0 Hz, 1H), 7.05 (m, 2H), 7.34 (m, 2H), 7.47 (d, J=3.0 Hz, 1H), 7.79 (m, 1H), 7.90 (d, J=3.3 Hz, 1H).

ANTI-HEPATITIS VIRUS EXPERIMENTAL EXAMPLES

Antiviral Experimental Example 1

Anti-Hepatitis B Virus (HBV) Activity Assay

1. Object for Experiment:

The anti-HBV activity assay of a specimen compound was performed in HepG2.2.15 cells stably transformed with the whole genome of HBV, including the determination of the cytotoxicity of the specimen compound (CC$_{50}$) and the effect of the specimen compound on the replication level of HBV-DNA (IC$_{50}$).

2. Principle for Experiment:

The Human hepatoma carcinoma cell HepG2.2.15 cell line stably transformed with the whole genome of HBV can stably secrete hepatitis B virosomes (containing DNA) in the supernatant of culture during culture. Both the antiviral activity and the cytotoxicity of the specimen drugs may be determined by detecting the amount of virus DNA secreted into the supernatant of culture by the cells under the intervention of an antiviral drug, in reference to the amount in control group that is the absence of the antiviral drug. A real-time fluorescent quantitation PCR assay was adopted to determine the concentration of a specimen drug at which 50% of the replication of HBV-DNA was inhibited (IC$_{50}$), and a MTT assay was adopted to determine the concentration of a specimen drug at which 50% cytotoxicity occurs (CC$_{50}$).

3. Preparation of Samples for Experiment:

The specimen drug was prepared into a solution having a concentration (400 μM) desired for the experiment before use. Six diluted concentrations were tested for each specimen drug. The clinical anti-hepatitis B virus drug Lamivudine was used as the positive control in experiment so as to determine whether the reaction is normal or not in each experiment.

4. Experimental Protocol:

a) Experimental Method and Collection of the Supernatant of Culture

HepG2.2.15 cells were inoculated on a 96-well plate at 5×10⁵ cells/ml. On the second day, the specimen drug was added. After the culture medium and the specimen drug having the same concentration as above were replaced periodically, on the eighth day, the supernatant of culture was collected to be tested. To the cells on the 96-well plate, MTT (5 mg/ml) is added. 4 hours later, MTT lysis solution was added (100 µl/well). The next day, $OD_{570}$ was read on a microplate reader. The cytotoxicity of the specimen drug on HepG2.2.15 cells, the influence of specimen drug on cell growth, and the concentration of specimen drug at which 50% of cells were killed ($CC_{50}$) were calculated in accordance with the OD value.

b) Determination of the Amount of HBV-DNA in the Supernatant of Culture Using a Fluorescent Quantitation PCR Assay A proper amount of the supernatant of culture was added into an isovolumic virus extract and mixed uniformly. The resulted mixture was boiled, and then centrifuged for 5 minutes at 10,000 rpm at room temperature. A proper amount of the obtained supernatant was used to perform PCR amplification, and meanwhile four standard samples of HBV-DNA were set up to make a standard curve. The inhibition of each specimen drug at various concentrations against the replication of HBV-DNA was calculated according to the detected replication value of the viral DNA, and then the half inhibition of the specimen drug was calculated to obtain its $IC_{50}$.

```
Primers for PCR Experiment:
P1: 5'ATCCTGCTGCTATGCCTCATCTT3'

P2: 5' ACAGTGGGGAAAGCCCTACGAA3'.

Probe for PCR Experiment:
5'TGGCTAGTTTACTAGTGCCATTTTG3'
```

4. Experimental Results:

TABLE 1

Anti-HBV Activity Assay of Compounds

| Compound | $IC_{50}$(µM) | $CC_{50}$(µM) | SI |
|---|---|---|---|
| 391-1 | 1.63 | 34 | 20.9 |
| 391-2 | 5.4 | >100 | >18.5 |
| 391-3 | <0.41 | >100 | >243.9 |
| 393-1 | <0.41 | >33.3 | >81 |
| 393-2 | 0.41~33.3 | >33.3 | <81 |
| 373 | 0.9 | >100 | >111.1 |
| 389 | 30.2 | >100 | >3.3 |
| 391-F | 12.5 | >100 | >8 |
| 405-1 | 2.6 | >33.3 | >12.8 |
| Me-373 | 1.1 | >100 | >90.9 |
| Me-391-1 | 2.9 | >33.3 | >11.5 |
| Me-393-1 | 0.2 | >100 | >500 |
| W28F | 2.6 | >33.3 | >12.8 |
| Lamivudine | <0.16 | >5 | >32 |

Note:
$CC_{50}$ is the concentration of a specimen drug at which 50% of cells was killed, representing the influence of the drug on the growth of HepG2.2.15 cells.
$IC_{50}$ is the concentration of a specimen drug at which 50% of the replication of HBV was inhibited.
SI is the bioactivity selective index of a specimen drug, and a SI value of greater than 2 means that the drug is effective, and the larger the SI value is, the more effective the drug will be.

5. Results and Discussions:

The results of the positive control (Lamivudine) revealed that the present testing method and experimental results are reliable. It can be seen from the above testing results at cellular level that the obtained compounds of the present invention maintain well the excellent bioactivity of this class of compounds against the replication of HBV-DNA, have an activity of anti-HBV replication comparable to that of W28F (N-parafluorobenzyl-5-isobutyl-2',2-bithiazole-4-formamide) and an half effective inhibition constant ($IC_{50}$) of 0.2-33.3 µM.

Antiviral Experimental Example 2

Activity Assay Against the Replication of Hepatitis C Virus (HCV)

1. Experimental Protocol:

The anti-HCV activity assay was performed by using Huh7.5.1 cells (donated by WUHAN INSTITUTE of VIROLOGY, CHINESE ACADEMY OF SCIENCES) infected by HCV (J399E) inserted with enhanced green fluorescent protein (EGFP). The variation of the green fluorescence intensity was recorded on a microplate reader and cytotoxicity was measured at the same time, so as to evaluate the influence of the compound on the replication activity of HCV.

Compounds to be tested were dissolved in DMSO to prepare a stock solution before the test. Upon using, the stock solution was diluted to a desired concentration with DMEM (Dulbecco's Modified Eagle Media, purchased from Gibco-BRL company (Life Technologies, Grand Island, N.Y., USA)) containing 10% FBS (fetal bovine serum, purchased from Hyclone company (Logan, Utah, USA)). The final concentration of DMSO for cell culture was less than 0.25% (V/V, Volume to Volume), and under such DMSO concentration the growth of cells would not be affected.

Positive control: ribavirin (purchased from Sigma/Aldrich). It was dissolved in DMSO to prepare a stock solution and stored at −20° C. before use, and diluted to a desired concentration upon using.

Huh7.5.1 cells (10% FBS, DMEM) at the concentration of 10⁵ cells/ml were inoculated on a 96-well plate (Costar 3904) with 100 µl per well. 24 hours later, the supernatant of culture was sucked out, and 50 µl of virus supernatant with MOI=0.1 was added. 8 hours later, 50 µl of the testing drug was added and 100 µl of culture medium was supplemented. After incubation for 72 hours, the supernatant was sucked out, and read on a fluorescent microplate reader (Ex=488 nm, Em=516 nm). Then each well was added with 20 µl of MTT (5 mg/ml) and additional 50 µl of culture medium. 4 hours later, 100 µl of MTT lysis solution was added. 6 hours later, reading was performed at a wavelength of 570 nm.

2. Experimental Results:

TABLE 2

Anti-Hepatitis C Virus (HCV) Activity Assay of Compounds

| Compound | $IC_{50}$(µM) | $CC_{50}$(µM) | SI |
|---|---|---|---|
| 391-1 | 10.2 | 48.6 | 4.8 |
| 391-2 | 21.3 | 134.3 | 6.3 |
| 391-3 | 9.9 | 28.1 | 2.8 |
| 393-1 | 7.4 | 40.9 | 5.5 |
| 393-2 | 1.5 | >33.3 | >22.2 |
| 373 | 5.7 | 85 | 14.9 |

TABLE 2-continued

Anti-Hepatitis C Virus (HCV) Activity Assay of Compounds

| Compound | IC$_{50}$(μM) | CC$_{50}$(μM) | SI |
|---|---|---|---|
| 389 | 6.6 | 76.5 | 11.6 |
| 391-F | 6.5 | 84.7 | 13.0 |
| 405-1 | 3.7 | 21.4 | 5.8 |
| Me-373 | 17.4 | 66.6 | 3.8 |
| Me-391-1 | 3.7 | >33.3 | >9 |
| Me-393-1 | 6.6 | >100 | >15.2 |
| Ribavirin | 72.4 | >200 | >2.8 |

Note:
CC$_{50}$ is the concentration of a specimen drug at which 50% of cells was killed, representing the influence of the drug on the growth of Huh7.5.1 cells.
IC$_{50}$ is the concentration of a specimen drug at which 50% of the replication of HCV was inhibited.
SI is the bioactivity selective index of a specimen drug, and a SI value of greater than 2 means that the drug is effective, and the larger the SI value is, the more effective the drug will be.

3. Results and Discussions:

The above results revealed that the in vitro administration of parts of the above representative compounds significantly inhibited the replication of HCV in the HCV-infected Huh7.5.1 cells, and the IC$_{50}$ of the above compounds ranges from 1.5 μM to 21.3 μM, which is superior to that of the positive control ribavirin.

Pharmacokinetic Experimental Example 3

In vivo Pharmacokinetic Studies in Rats

Research Protocol:

Intragastric Administration Three healthy male SD rats having body weights of 200 g to 250 g were administered with a specimen drug with a dosage of 20 mg/kg and a volume of 10 ml/kg. The rats were fasted for 12 hours before administration and had the freedom to drink water. The venous blood with a volume of 0.3 ml was obtained from the retrobulbar venous plexus of the rats at 0.25 h, 0.5 h, 1.0 h, 2.0 h, 3.0 h, 4.0 h, 5.0 h, 7.0 h, 9.0 h and 24 h after the administration, put in a heparinized tube, and centrifuged for 10 minutes at 3500 rpm to separate the plasma, which was stored at −20° C. to be tested.

Intravenous Injection: Three healthy male SD rats having body weights of 200 g to 250 g were administered with a specimen drug with a dosage of 10 mg/kg and a volume of 5.0 ml/kg. The rats were fasted for 12 hours before administration and had the freedom to drink water. The venous blood with a volume of 0.3 ml was obtained from the retrobulbar venous plexus of the rats at 5 min, 15 min, 0.5 h, 1.0 h, 2.0 h, 3.0 h, 4.0 h, 5.0 h, 7.0 h, 9.0 h and 24 h after the administration, put in a heparinized tube, centrifuged for 10 minutes at 3500 rpm to separate the plasma, which was stored at −20° C. to be tested.

Research Results:

After the dosage was normalized, W28F (10 mg/kg) had an average oral bioavailability of 2.80% calculated according to AUC$_{0-t}$. Under the same conditions, Compound 373 (20 mg/kg) had an average oral bioavailability of 6.9%, and Compound 391-2 (20 mg/kg) had an average oral bioavailability of 76.5%. Both Compound 373 and Compound 391-2 are superior to Compound W28F which is not substituted on its side chain.

What is claimed is:

1. A 2',2-bisthiazole non-nucleoside compound of formula I:

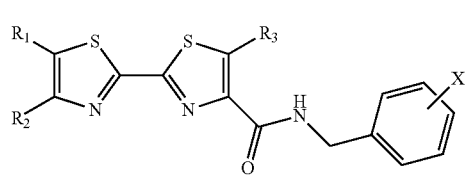

wherein,

R$_1$ and R$_2$ are each independently H or C$_1$-C$_4$ alkyl,

R$_3$ is C$_1$-C$_6$ alkyl substituted by at least one hydroxyl group, C$_1$-C$_6$ alkyl substituted by at least one C$_1$-C$_6$ alkoxyl group, C$_1$-C$_6$ alkyl substituted by at least one halogen atom, C$_2$-C$_6$ alkenyl, or C$_2$-C$_6$ alkenyl substituted by at least one hydroxyl group or at least one halogen atom, X is halogen atom.

2. The 2',2-bisthiazole non-nucleoside compound of claim 1, wherein R$_1$ is H, methyl or ethyl, and R$_2$ is H.

3. The 2',2-bisthiazole non-nucleoside compound of claim 1, wherein R$_3$ is C$_1$-C$_5$ alkyl substituted by one or two hydroxyl groups, C$_1$-C$_5$ alkyl substituted by one or two C$_1$-C$_4$ alkoxyl groups, C$_1$-C$_5$ alkyl substituted by one fluorine, chlorine or bromine atom, methylpropenyl, methylolpropenyl or fluoromethylpropenyl.

4. The 2',2-bisthiazole non-nucleoside compound of claim 1 wherein R$_3$ is C$_4$ alkyl substituted by one or two hydroxyl groups, C$_4$ alkyl substituted by one or two C$_1$-C$_4$ alkoxyl groups, C$_4$ fluoroalkyl, 2-methylpropenyl, 2-methylolpropenyl or 2-fluoromethylpropenyl.

5. The 2',2-bisthiazole non-nucleoside compound of claim 1 wherein X is F.

6. The 2',2-bisthiazole non-nucleoside compound of claim 1 which is one selected from the group consisting of

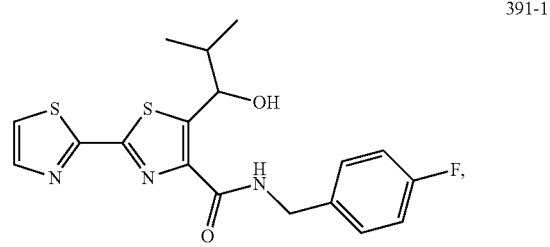

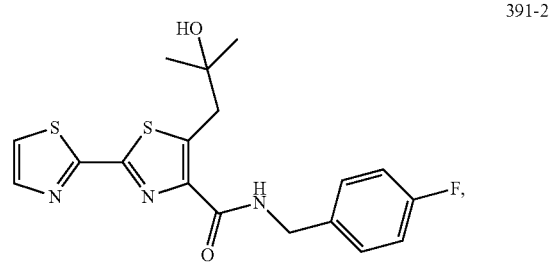

391-3
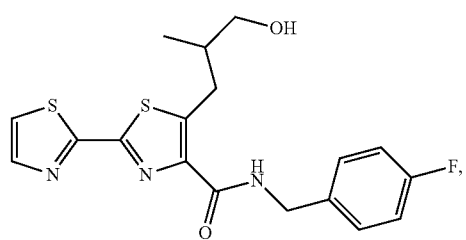
393-1
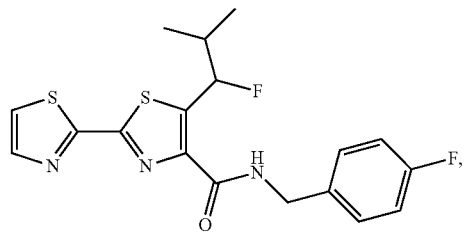
393-2
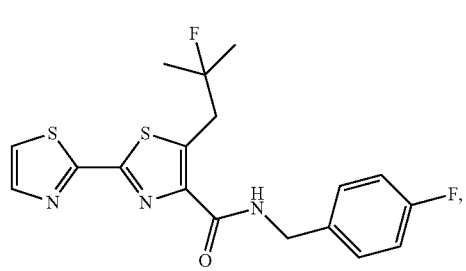
373
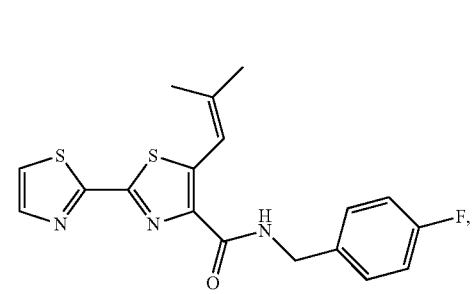
389
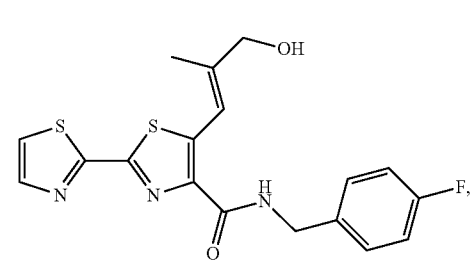
391-F
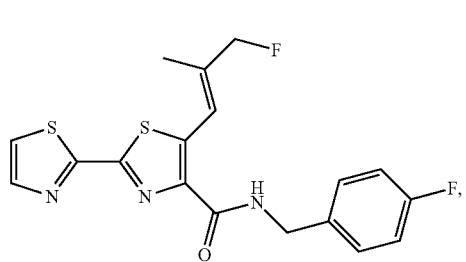
407
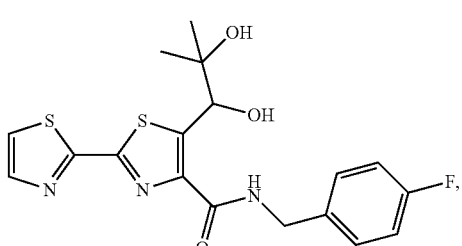
405-1
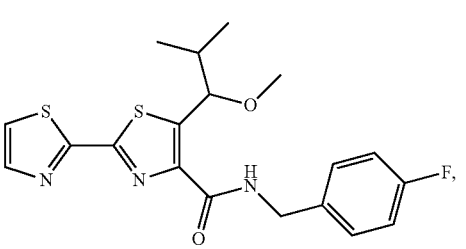
Me-373
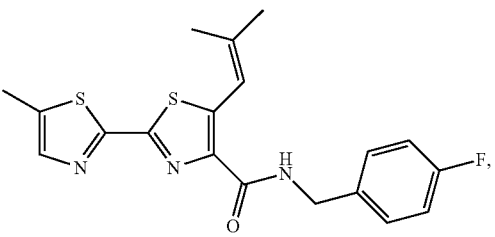
Me-391-1
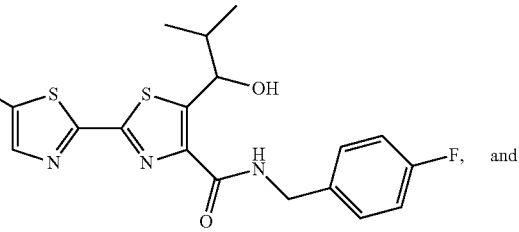
and
Me393-1
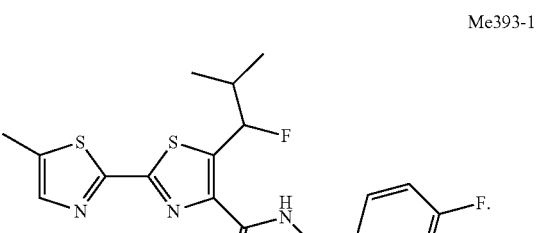

7. A method of preparing the 2',2-bisthiazole non-nucleoside compound of claim 1 following scheme III, scheme IV or scheme V:

Scheme III

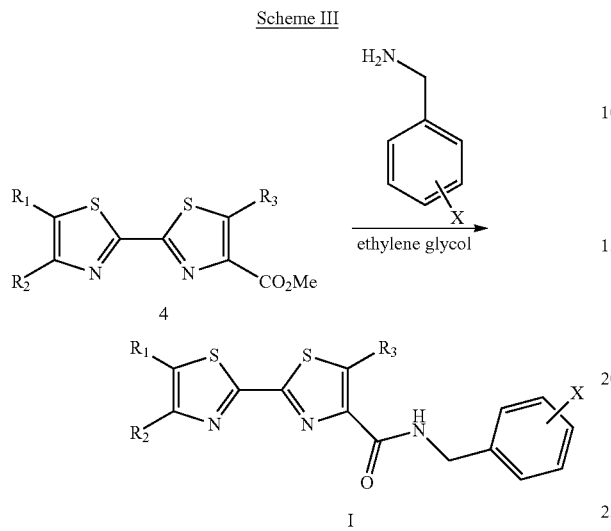

the intermediate methyl 2',2-bisthiazolecarboxylate 4 reacts with a halogenated benzylamine as a nucleophilic reagent in ethylene glycol as a solvent at an elevated temperature to produce the 2',2-bisthiazole non-nucleoside compound, or Scheme IV

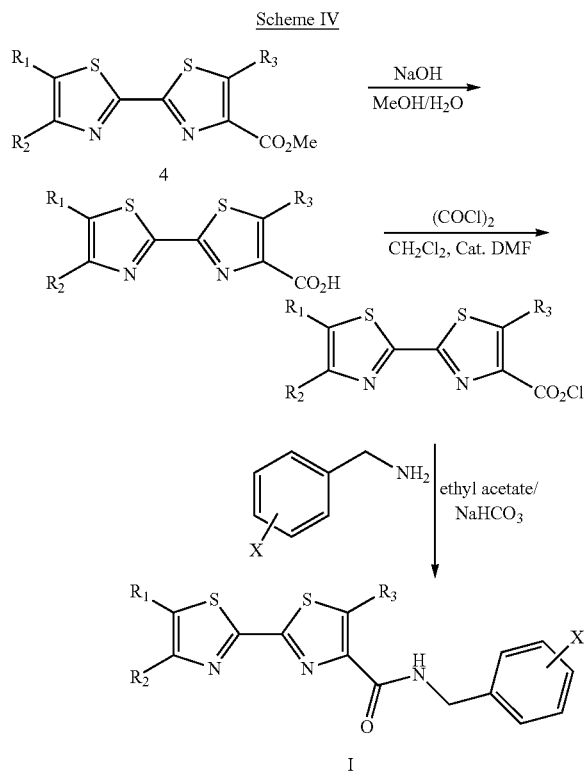

the intermediate methyl 2',2-bisthiazolecarboxylate 4 is converted through hydrolyzation into a corresponding acid, which reacts with oxalylchloride to produce an acyl chloride, and the acyl chloride then reacts with a halogenated benzylamine to produce the 2',2-bisthiazole non-nucleoside compound, or Scheme V

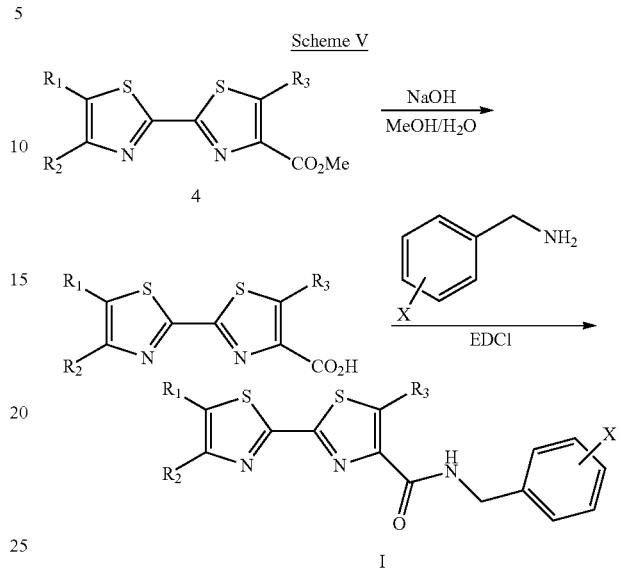

the intermediate methyl 2',2-bisthiazolecarboxylate 4 is converted through hydrolyzation into a corresponding acid, which reacts with a halogenated benzylamine in the presence of EDCI (1-ethyl-(3-dimethylaminopropyl) carbodiimide hydrochloride) as a condensing agent to produce the 2',2-bisthiazole non-nucleoside compound, wherein, the definitions of $R_1$, $R_2$, $R_3$ and X in above schemes are as defined in claim 1.

8. A pharmaceutical composition against viral hepatitis B and/or viral hepatitis C, which comprises a therapeutically effective amount of one or more of the 2', 2-bisthiazole non-nucleoside compounds according to claim 1 as an active component and optionally pharmaceutically acceptable common adjuvants.

9. A method of treating hepatitis B or hepatitis C, comprising:
administering to a subject suffering from hepatitis B or hepatitis C a therapeutically effective amount of the 2',2-bisthiazole non-nucleoside compound according to claim 1.

10. The 2',2-bisthiazole non-nucleoside compound of claim 2, wherein $R_3$ is $C_1$-$C_5$ alkyl substituted by one or two hydroxyl groups, $C_1$-$C_5$ alkyl substituted by one or two $C_1$-$C_4$ alkoxyl, groups, $C_1$-$C_5$ alkyl substituted by one fluorine, chlorine or bromine atom, methylpropenyl, methylolpropenyl or fluoromethylpropenyl.

11. The 2',2-bisthiazole non-nucleoside compound of claim 2, wherein $R_3$ is $C_4$ alkyl substituted by one or two hydroxyl groups, $C_4$ alkyl substituted by one or two $C_1$-$C_4$ alkoxyl groups, $C_4$ fluoroalkyl, 2-methylpropenyl, 2-methylolpropenyl or 2-fluoromethylpropenyl.

12. The 2',2-bisthiazole non-nucleoside compound of claim 5, wherein F is at 4-site.

13. The 2',2-bisthiazole non-nucleoside compound of claim 2, wherein X is F.

14. The 2',2-bisthiazole non-nucleoside compound of claim 13, wherein F is at 4-site.

15. The 2',2-bisthiazole non-nucleoside compound of claim 3, wherein X is F.

16. The 2',2-bisthiazole non-nucleoside compound of claim 15, wherein F is at 4-site.

17. The 2',2-bisthiazole non-nucleoside compound of claim 4, wherein X is F.

18. The 2',2-bisthiazole non-nucleoside compound of claim 17, wherein F is at 4-site.

* * * * *